US012213672B2

(12) United States Patent
Yuasa et al.

(10) Patent No.: US 12,213,672 B2
(45) Date of Patent: Feb. 4, 2025

(54) CLIP DEVICE FOR ENDOSCOPE

(71) Applicant: OLYMPUS MEDICAL SYSTEMS CORP., Tokyo (JP)

(72) Inventors: Masaru Yuasa, Hachioji (JP); Yoshitsugu Uekusa, Hachioji (JP); Shinya Ansai, Hachioji (JP); Takushi Haramaki, Hachioji (JP); Shogo Shindo, Koganei (JP)

(73) Assignee: Olympus Medical Systems Corp., Tokyo (JP)

( * ) Notice: Subject to any disclaimer, the term of this patent is extended or adjusted under 35 U.S.C. 154(b) by 385 days.

(21) Appl. No.: 17/668,457

(22) Filed: Feb. 10, 2022

(65) Prior Publication Data
US 2022/0265274 A1  Aug. 25, 2022

Related U.S. Application Data

(60) Provisional application No. 63/148,655, filed on Feb. 12, 2021.

(51) Int. Cl.
*A61B 17/08*  (2006.01)
*A61B 17/00*  (2006.01)

(52) U.S. Cl.
CPC ...... *A61B 17/083* (2013.01); *A61B 17/00234* (2013.01); *A61B 2017/088* (2013.01)

(58) Field of Classification Search
CPC ............ A61B 17/083; A61B 17/00234; A61B 2017/088
See application file for complete search history.

(56) References Cited

U.S. PATENT DOCUMENTS 5,156,609 A * 10/1992 Nakao ............... A61B 17/10
606/205
2006/0155308 A1  7/2006 Griego

FOREIGN PATENT DOCUMENTS

| JP | 2002-345828 A | 12/2002 |
| JP | 2008-526376 A | 7/2008 |
| JP | 2012-166003 A | 9/2012 |
| JP | 2013-135864 A | 7/2013 |
| JP | 2020-185036 A | 11/2020 |
| KR | 10-2018-0087740 A | 8/2018 |

(Continued)

OTHER PUBLICATIONS

Office Action dated Dec. 20, 2022, issued in corresponding Japanese Patent Application No. 2022-018973.

(Continued)

*Primary Examiner* — Shaun L David
*Assistant Examiner* — Rachael L Geiger
(74) *Attorney, Agent, or Firm* — Morgan, Lewis & Bockius LLP

(57) ABSTRACT

A clip device includes a sheath having a lumen with at least one open end and a plurality of clip arms movable between a first configuration in which the plurality of clip arms are opened to receive a target tissue, and a second configuration in which the plurality of clip arms are closed to grip the target tissue. Locking mechanisms respectively provided on the plurality of clip arms engage one another for maintaining the second configuration. A restraining mechanism is optionally configured to be associated with the locking mechanisms to prevent the target tissue from being pinched between the locking mechanisms.

18 Claims, 16 Drawing Sheets

(56) References Cited

FOREIGN PATENT DOCUMENTS

| | | |
|---|---|---|
| WO | 2018/057370 A1 | 3/2018 |
| WO | 2019/189864 A1 | 10/2019 |
| WO | 2020/095427 A1 | 5/2020 |

OTHER PUBLICATIONS

Office Action dated Aug. 28, 2024, issued in related U.S. Appl. No. 17/677,219.

\* cited by examiner

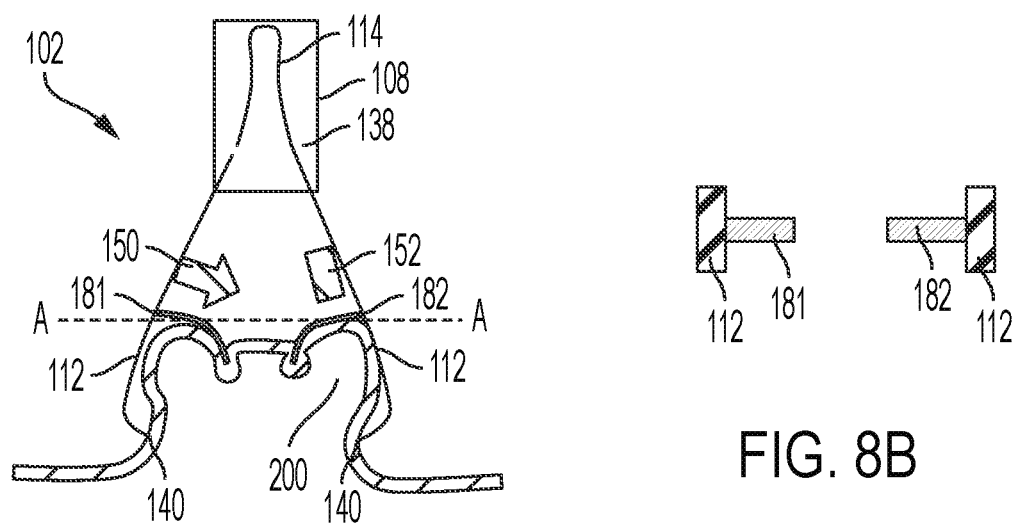
FIG. 8A
FIG. 8B
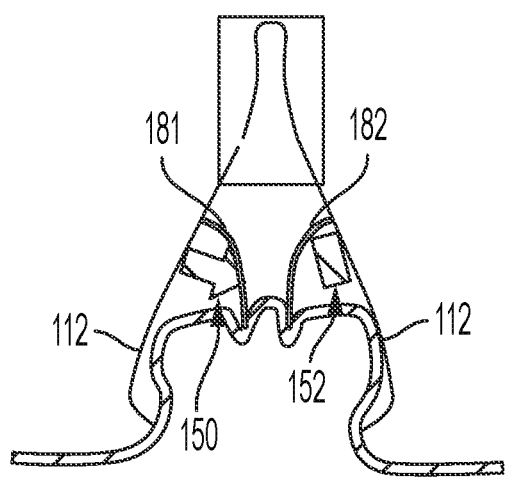
FIG. 8C

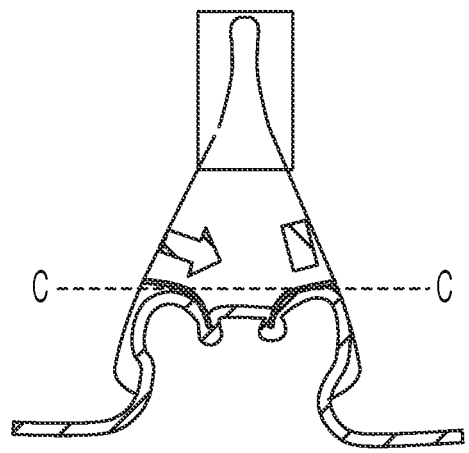
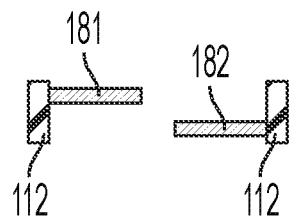
FIG. 10A
FIG. 10B
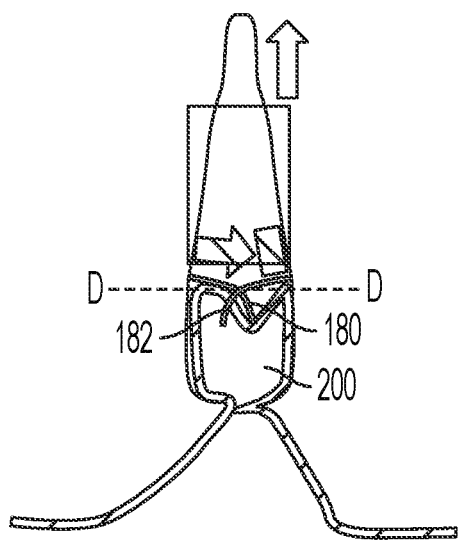
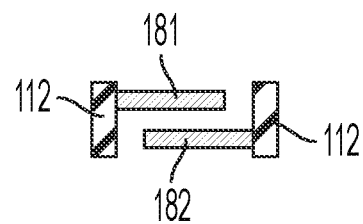
FIG. 11A
FIG. 11B

CLIP DEVICE FOR ENDOSCOPE

RELATED APPLICATION DATA

This application is based on and claims priority under 35 U.S.C. § 119 to U.S. Provisional Application No. 63/148,655, filed Feb. 12, 2021, the entire contents of which are incorporated herein by reference.

FIELD OF THE INVENTION

The present invention relates to a clip device for an endoscope, and more particularly, to an endoscopic clip device with an improved mechanism for locking the clip arms of the clip device.

DESCRIPTION OF THE RELATED ART

Various endoscopic clip devices have been known, many of which require hemostasis clips to control internal bleeding. The hemostasis clips grasp tissue surrounding a wound and hold edges of the wound together temporarily to allow natural healing processes to permanently close the wound. Specialized endoscopic clip devices are used to deliver the hemostasis clips at the desired locations within the body after which the endoscopic clip delivery device is withdrawn, leaving the hemostasis clips within the body. Such a conventional endoscopic clip device may be loaded onto a distal end of an applicator assembly prior to an endoscopic procedure. Once a hemostasis clip has been deployed at a desired target area in the body, the applicator assembly may be reloaded with a new clip unit.

The conventional endoscopic clip device includes a pair of clip arms, proximal ends of which are connected to a connector that is configured to releasably engage a distal end of a control member of an applicator. The clip arms include respective locking mechanisms to lock the clip arms when a target tissue is gripped, such that the clip arms may be drawn toward one another until the locking mechanisms engage one another. Once the clip arms have been locked, a proximal force beyond a predetermined threshold value may be exerted on the control member, disengaging the control member from the connector so that the control member may be coupled to a new clip unit.

However, the locking mechanisms of the conventional endoscopic clip device are deficient in one or more ways. For example, when the conventional locking mechanisms are moved to lock the clip arms, the target tissue may be pinched between the locking mechanisms. In this situation, the locking mechanism cannot function properly, thereby causing an undesirable hemostasis procedure.

SUMMARY OF THE INVENTION

Accordingly, the present disclosure is directed to an endoscopic clip device and clip unit, which substantially obviate one or more of the issues due to limitations and disadvantages found in conventional endoscopic clip devices and clip units.

An object of the present disclosure is to provide a clip device, which comprises a sheath having a lumen with at least one open end and a plurality of clip arms movable between a first configuration in which the plurality of clip arms are opened to receive a target tissue, and a second configuration in which the plurality of clip arms are closed to grip the target tissue. Locking mechanisms respectively provided on the plurality of clip arms engage one another for maintaining the second configuration. A restraining mechanism is optionally configured to be associated with the locking mechanisms to prevent the target tissue from being pinched between the locking mechanisms.

Another object of the present disclosure is to provide an endoscopic clip device system for treating tissue, which comprises a clip unit including a pair of clip arms, a proximal end of the clip arms connected to a connector, the clip unit movable between a first configuration, in which distal ends of the clip arms are separated from one another to receive a target tissue therebetween, and a second configuration, in which the target tissue is gripped by the clip arms; locking mechanisms respectively disposed on the clip arms for locking the clip arms in the second configuration; an applicator including a sheath and a control member extending therethrough, the sheath extending from a proximal end to a distal end and including a lumen extending therethrough, the control member extending from a proximal end to a distal end configured to be releasably coupled to the connector to move the clip unit between the first configuration and the second configuration, the clip arms being constrained toward the second configuration via a surface of the lumen when the clip arms are drawn proximally thereinto; and a restraining structure configured to operate associated with the clip unit to prevent the target tissue from being pinched between the locking mechanisms.

Still another object of the present disclosure is to provide a method of delivering an endoscopic clip device, which comprises loading a first clip unit on an applicator by coupling a control member of the applicator to a connector at a proximal end of clip arms of the first clip unit; inserting the first clip unit to a target site within a patient via a channel of an endoscope; moving the first clip unit between a first configuration, in which distal ends of the clip arms are separated from one another, and a second configuration, in which the distal ends of the clip arms are drawn toward one another, by moving the control member longitudinally until a target tissue is gripped between the distal ends of the clip arms; locking the clip arms in the second configuration by drawing the control member further proximally until the clip arms engage one another via a locking mechanism thereof; and releasing the first clip unit from the applicator by drawing the control member even further proximally until a proximal force exerted on the connector by the control member exceeding a predetermined threshold value so that the control member disengages from the connector to release the clip assembly from the applicator, wherein, in the second configuration, when the clip arms are drawn toward one another, a restraining mechanism is operated to prevent the target tissue from being pinched between the locking mechanisms.

Additional features and advantages will be set forth in the description that follows, and in part will be apparent from the description, or may be learned by practice of the invention. The objectives and other advantages of the disclosed an endoscopic clip device, system and method will be realized and attained by the structure particularly pointed out in the written description and claims thereof as well as the appended drawings.

BRIEF DESCRIPTION OF THE DRAWINGS

The following detailed description of preferred embodiments can be read in connection with the accompanying drawings in which like numerals designate like elements.

FIG. 8A is a front view schematically illustrating a clip unit in a first configuration in which a pair of clip arms are opened to receive a target tissue according to an exemplary embodiment, FIG. 8B is a magnified cross-sectional view taken line A-A of FIG. 8A, FIG. 8C is a front view schematically illustrating a clip unit in the first configuration in which restraining members are located on the pair of clip arms more proximally than locking members according to an exemplary embodiment.

FIG. 10A is a front view schematically illustrating a clip unit in a first configuration in which a pair of clip arms are opened to receive a target tissue according to another exemplary embodiment, and FIG. 10B is a magnified cross-sectional view taken line C-C of FIG. 10A.

FIG. 11A is a front view schematically illustrating a clip unit in a second configuration in which the target tissue is gripped by the pair of clip arms are according to another exemplary embodiment, and FIG. 11B is a cross-sectional view taken line D-D of FIG. 11A.

Figure 1:
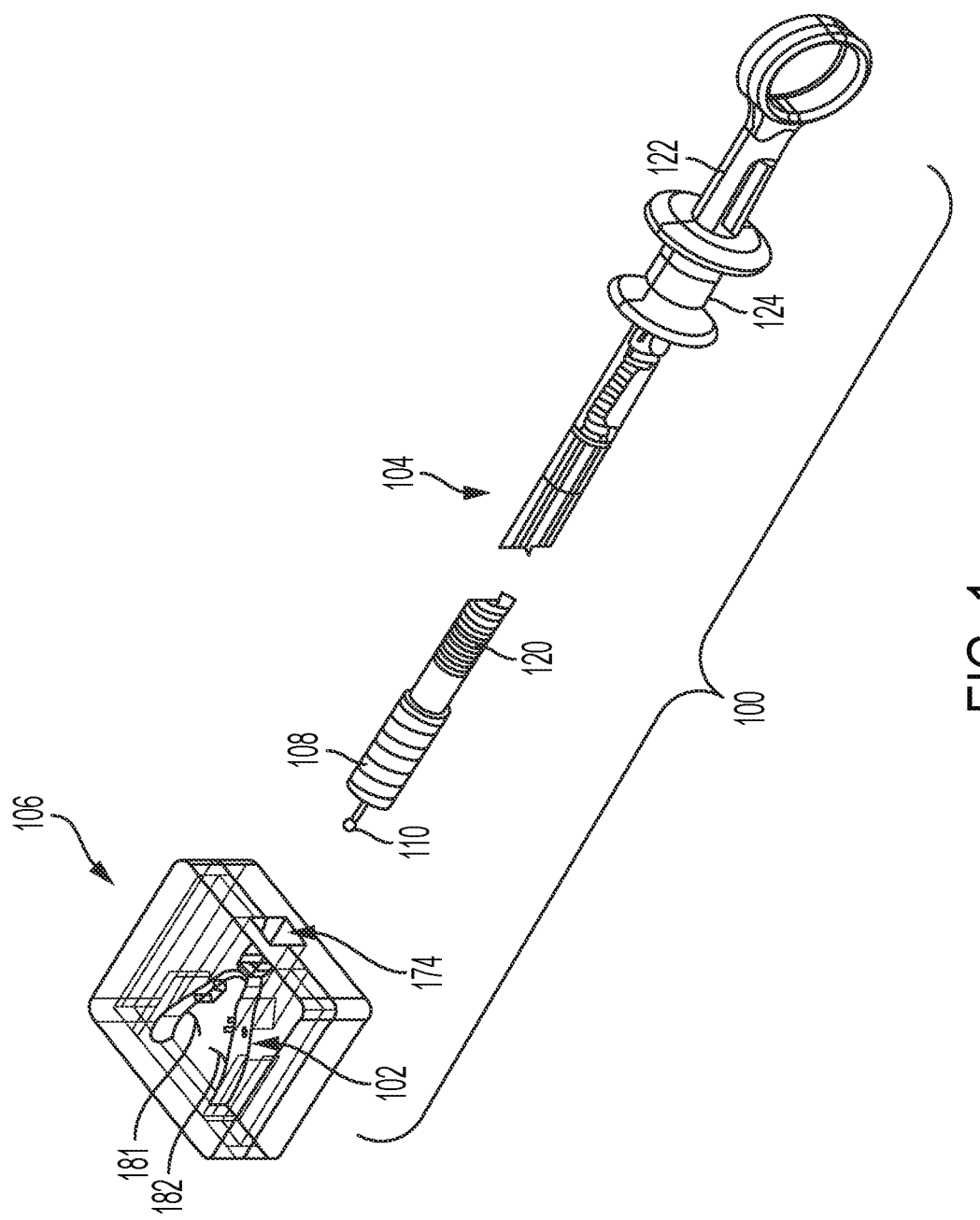
FIG. 1 shows a perspective view of a system according to an exemplary embodiment of the present invention.

Throughout all of the drawings, dimensions of respective constituent elements are appropriately adjusted for clarity. For ease of viewing, in some instances only some of the named features in the figures are labeled with reference numerals.

DETAILED DESCRIPTION

Hereinafter, accompanying drawings, which are incorporated in and constitute a part of the specification, illustrate exemplary embodiments of the invention, and together with the general description given above and the detailed description of the exemplary embodiments given below, serve to explain the principles of the invention.

Also, it should be noted that the terms "proximal" and "proximally" as used herein, are intended to refer to a direction toward (proximal/proximally) a user of the device, and the terms "distal" and "distally" as used herein, are intended to refer to a direction away from (distal/distally) the user of the device. The term "patient," as used herein, comprises any and all organisms and includes the term "subject." A patient can be a human or an animal.

Figure 2:
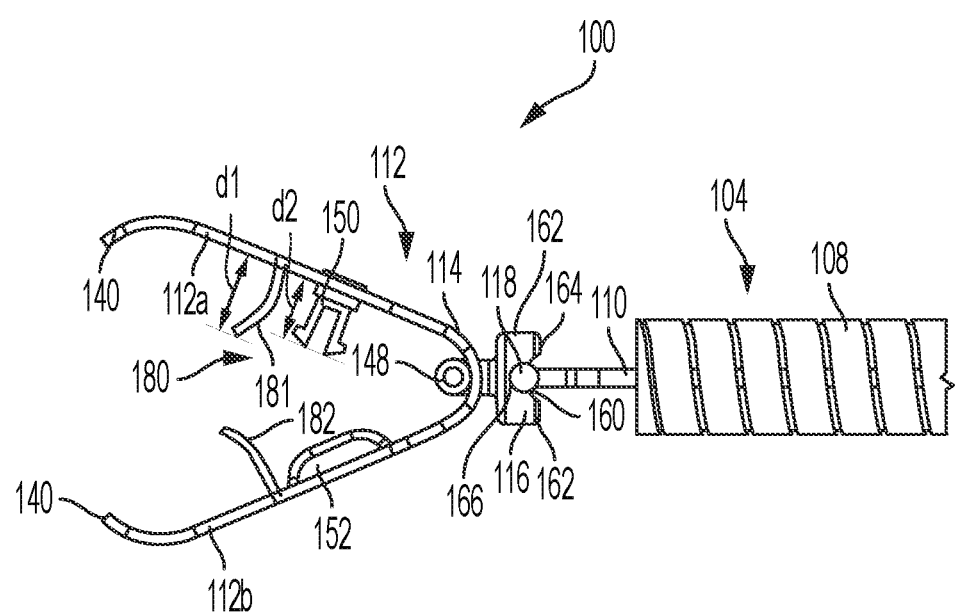
FIG. 2 shows a side view of a distal portion according to the system of FIG. 1.
Figure 3:
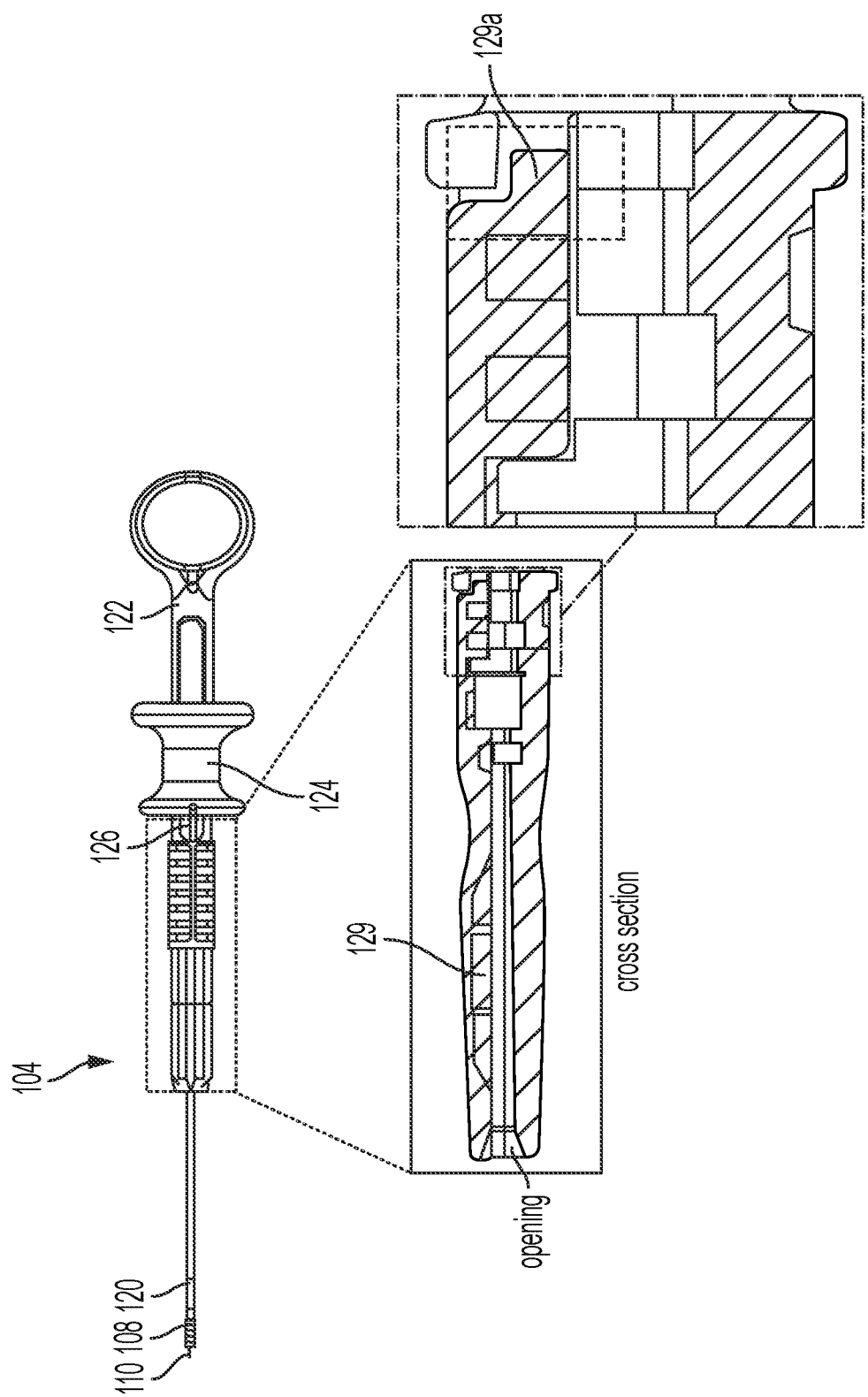
FIG. 3 shows a side view of an applicator according to the system of FIG. 1.

FIG. 1 shows a perspective view of an exemplary clip device system 100 and FIG. 2 shows a side view of a distal portion of the exemplary clip device system 100. As shown in FIGS. 1 and 2, the clip device system 100 comprises a clip unit 102, an applicator 104 and a cartridge 106. The clip unit 102 is loadable into a distal portion of the applicator 104 before the system 100 is inserted into a living body to clip a target tissue. The applicator 104 is configured such that, after deployment of the clip unit 102 in the body of a patient, a new clip unit 102 may be loaded onto the applicator 104 so that the same applicator 104 may be used to deliver a new clip unit 102 to a second portion of the target tissue in the patient. Each clip unit 102 according to this embodiment may be stored in the cartridge 106, which facilitates loading of the clip unit 102 onto the applicator 104.

Specifically, as shown in FIG. 1, prior to being loaded on the applicator 104, the clip unit 102 is stored in the cartridge 106, which may be configured, for example, as a storage container so that the clip unit 102 may be securely stored therein. In one embodiment, the clip unit 102 may be stored in the cartridge 106 in a first configuration (tissue receiving configuration). The cartridge 106 includes a proximal opening 174 through which a distal portion of the applicator 104 (e.g., a distal end of the control member 110 and a distal end of the sheath 108) may be inserted into the cartridge 106 to load the clip unit 102 thereon. Once the distal end 118 of the control member 110 has been coupled to the connector 116 of the clip unit 102, the clip unit 102 may be drawn toward a second configuration (tissue gripping configuration) to remove the clip unit 102 from the cartridge 106.

The applicator 104 includes a sheath 108 at a distal end thereof and a control member 110 extending therethrough. The clip unit 102 includes a pair of clip arms 112 including a proximal end 114 connected to a connector 116 that is configured to releasably engage a distal end 118 of the control member 110. Once the clip unit 102 has been connected to the control member 110, the clip unit 102 may be moved with respect to the sheath 108 between a first configuration, which is a tissue receiving configuration in which the pair of clip arms 112 are opened to receive a target tissue, and a second configuration, which is a tissue gripping configuration in which the target tissue is gripped by the pair of clip arms 112.

As shown in FIGS. 3-7, the applicator 104 includes the sheath 108, a flexible member 120 extending proximally therefrom, and the control member 110 extending through the sheath 108 and the flexible member 120. A proximal end of the flexible member 120 is connected to a handle member 122, which includes an actuator such as, for example, a spool 124, coupled thereto. In one example, the spool 124 is connected to a proximal end 126 of the control member 110 so that, once the clip unit 102 is loaded onto the applicator 104, the spool 124 may be slid longitudinally over the handle member 122 to move the clip unit 102 between the first configuration (tissue receiving configuration) and the second configuration (tissue gripping configuration). Specifically, sliding the spool 124 over the handle member 122 moves the control member 110, and thereby the clip unit 102, relative to the sheath 108 to move the clip unit 102 between the first and second configurations.

Figure 6:
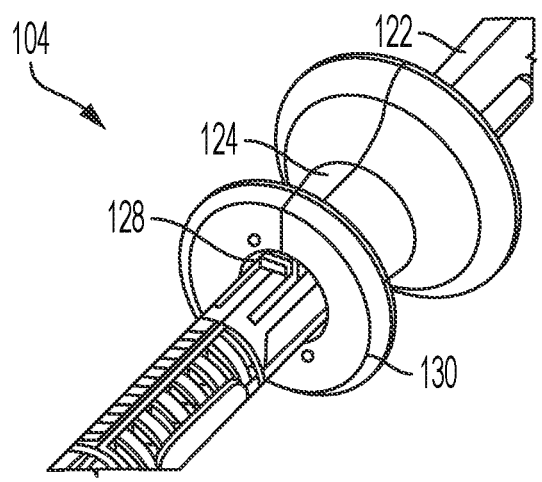
FIG. 6 shows a perspective view of a portion of the applicator of FIG. 3.
Figure 7:
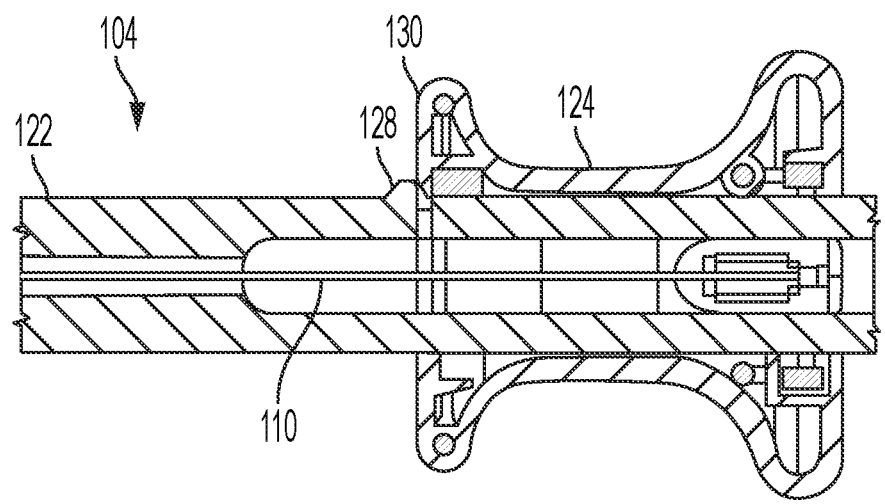
FIG. 7 shows a longitudinal cross-sectional view of the portion of the applicator of FIG. 6.

In one embodiment, as shown in FIGS. 6-7, the handle member 122 includes a positioning feature 128 interfacing with the spool 124 to provide tactile feedback to a user of the exemplary clip device system 100 regarding a position of the connector 116 with respect to the sheath 108. The positioning feature 128 may include a deformable protrusion extending laterally outward from an exterior surface therefrom. The protrusion is deformable so that the spool 124 may be slid thereover when a force exerted thereon exceeds a predetermined threshold value. The spool 124 may be slid thereover during initial loading of the clip unit 102. However, when a distal surface 130 of the spool 124 abuts a portion of the protrusion, the positioning feature 128 provides a tactile feedback to the user indicating that the connector 116 is at a distal-most position with respect to the sheath 108, without extending entirely distally past the sheath 108. In other words, the clip unit 102 is at a maximum open configuration without extending entirely out of the sheath 108 (e.g., separated from the sheath 108).

Moreover, a part of the handle member 122 may be cut off to form a recess portion, and a lid member 129, which is a roof-shaped cover, may be detachably fit into the handle member 122 to cover the recess portion. The lid member 129 has a projection 129a formed at a proximal end of the lid member 129. The projection 129a is configured to engage with the positioning feature 128 so that the lid member 129 is prevented from coming off the handle member 122.

The flexible member 120 (e.g. in FIGS. 1 and 3) may be formed as a coil of wire through which the control member 110 extends from the distal end 118 to the proximal end 126. As would be understood by those skilled in the art, the coil of wire preferably has sufficient flexibility to be passed through even tortuous paths of living body and, in this exemplary embodiment, is sized and shaped to permit it to be passed through a channel of an endoscope or other insertion device. Although the flexible member 120 is shown and described as a coil of wire, it will be understood by those of skill in the art that any other suitable flexible structure may be employed so long as the flexible member 120 is capable of providing a force in compression sufficient to counter the tension to be placed on the control member 110 from the clip unit 102. Although the applicator 104 is described as including the spool 124, the applicator 104 may include any of a variety of actuating mechanisms for moving the control member 110 to control movement of the clip arms 112.

The control member 110 extends from the distal end 118 releasably coupled to the connector 116 to the proximal end 126 connected to the spool 124. The distal end 118 is sized and shaped to be releasably coupled to a corresponding feature of the connector 116. In one embodiment, the distal end 118 may be shaped as an enlarged ball that is received within a correspondingly shaped socket of the connector 116. It will be understood by those of skill in the art, however, that the distal end 118 may have any of a variety of shapes and sizes so long as the distal end 118 is releasably coupleable with the connector 116.

As shown in FIG. 2, the connector 116 includes a distal end 148 connected to the proximal end 114 and extends proximally therefrom to receive the distal end 118 of the control member 110 therein. The connector 116 includes a longitudinal slot 160 defined via opposed portions 162 that are spreadable to receive the distal end 118 of the control member 110. The longitudinal slot 160 extends from a proximal opening 164 to a space 166 sized and shaped to receive the distal end 118. In one exemplary embodiment, the distal end 118 may be configured as a ball received within a correspondingly sized and shaped socket of the space 166. The proximal opening 164 of the slot 160 has a smaller cross-sectional area (e.g., diameter) than a cross-sectional area of the space 166. The opposed portions 162 are spreadable to receive the distal end 118 of the control member 110 and biased toward one another so that, once the distal end 118 passes distally into the space 166, the opposed portions 162 spring back to lock the distal end 118 within the space 166, coupling the control member 110 to the connector 116. Thus, longitudinal movement of the control member 110 relative to the sheath 108 may control movement of the clip arms 112 between the tissue receiving and the tissue clipping configurations.

According to this embodiment, the distal end 118 of the control member 110 may be inserted into the connector 116 via the proximal opening 164. When the control member 110 is pushed distally into the connector 116 beyond a predetermined threshold value, the proximal opening 164 of the longitudinal slot 160 deforms to permit the distal end 118 to be passed through the proximal opening 164 into the space 166. In one embodiment, opposed portions 162 defining the longitudinal slot 160 may be separated from one another to permit the distal end 118 to be passed through the proximal opening 164 into the space 166. Once the distal end 118 is received within the space 166, the longitudinal slot 160 reverts to its original size, holding the distal end 118 of the control member 110 therein.

Figure 4:
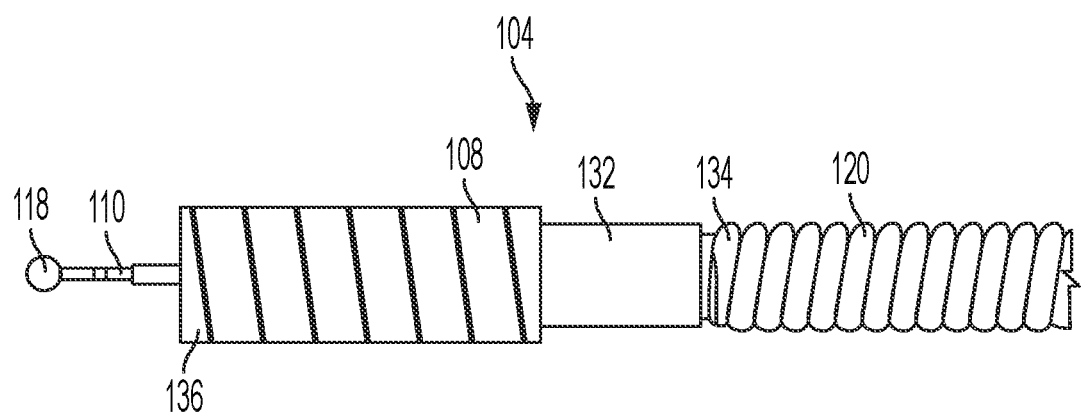
FIG. 4 shows a side view of a distal portion of the applicator of FIG. 3.
Figure 5:
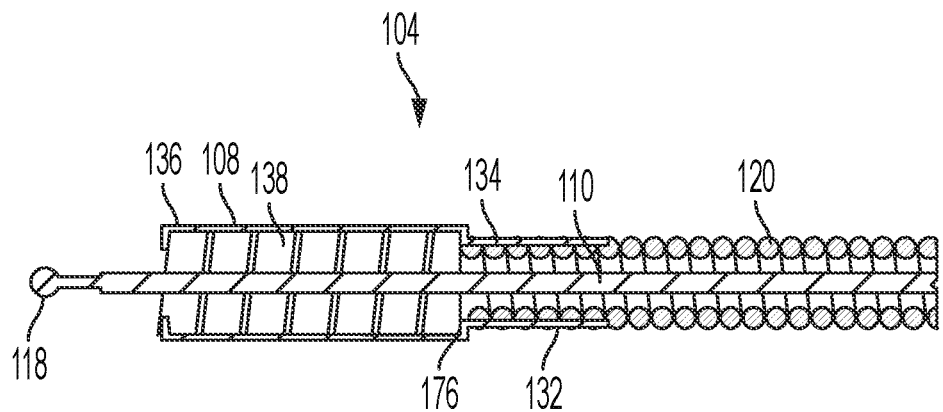
FIG. 5 shows a longitudinal cross-sectional view of the distal portion of FIG. 4.

As shown in FIGS. 4 and 5, the sheath 108 extends longitudinally from a proximal end 132 connected to a distal end 134 of the flexible member 120 to a distal end 136 and including a lumen 138 extending therethrough. The lumen 138 may be sized and shaped to receive at least a portion of the clip unit 102 therein. The lumen 138 includes a shoulder 176 along a proximal portion thereof which reduces a cross-sectional area of the lumen 138 proximally thereof so that, the connector 116 is prevented from passing proximally past the shoulder 176. The sheath 108 may be configured as a hypotube attached to the distal end 134 of the flexible member 120. The sheath 108 may be laser cut to increase a flexibility thereof. For example, the sheath 108 may include a helically extending cut therealong so that the sheath 108 may be flexed along a length thereof. Moreover, the sheath 108 may be such a coil sheath that is configured to include a PTFE tube provided between the coil sheath and stranded wires of multiple metal wires inserted through the sheath 108. The stranded wires of multiple metal wires may be coated by silicon as a lubricant.

As shown in FIG. 2, the clip unit 102 includes the pair of clip arms 112, which have a proximal end 114 connected to the connector 116. In one embodiment, the pair of clip arms 112 may be formed of a single piece of material bent in half at the proximal end 114 to form the two clip arms 112. The connector 116 may be connected to the single piece of material at the point at which the material bends (e.g., the proximal end 114) to form the two clip arms 112. Although the clip arms 112 are described and shown as being formed of the single piece of material, the pair of clip arms 112 may be formed via two separate pieces of material, proximal ends of which are connected to one another via the connector 116.

The clip arms 112 of this embodiment are biased so that distal ends 140 thereof move apart from one another into an open tissue receiving configuration when not drawn into the sheath 108. When drawn into the sheath 108, the sheath 108 constrains the clip arms 112, holding the distal ends 140 thereof together in a closed tissue gripping configuration. The connector 116 is longitudinally slidable with the lumen 138 of the sheath 108 to move the clip arms 112 between the tissue receiving configuration and the tissue gripping configuration. The distal ends 140 of each of the clip arms 112 may project laterally inward toward the distal end 140 of the other of the clip arms 112 to facilitate gripping of target tissue therebetween. The distal ends 140 may further include other gripping features such as, for example, teeth and/or protrusions.

The clip arms 112 may include locking mechanisms to lock the pair of clip arms when the clip unit 102 is in the closed tissue gripping configuration. In this exemplary embodiment, as shown in FIG. 2, the locking mechanisms include corresponding mating features 150, 152 (a pair of locking members) for locking the clip arms 112 in the closed tissue gripping configuration. A first one of the clip arms 112 includes a male lock feature 150 while a second one of the clip arms 112 includes a female lock feature 152. In particular, the male lock feature 150 is disposed on and extends from an inner surface of the first one of the clip arms 112 toward the second one of the clip arms 112 and includes a pair of prongs. The female mating feature 152 is disposed on and extends from an inner surface of the second one of the clip arms 112 toward the first one of the clip arms 112. The female mating feature 152 includes an opening that is sized and shaped to permit the pair of prongs to be received therein.

Additionally, on each arm, the restraining mechanism and the locking mechanism extend in a direction away from the arm different distances. For example and as shown in FIG. 2, restraining member 181 of the restraining mechanism extends a first distance d1 in a first direction away from the first arm 112a and mating feature 150 of the locking mechanism extends a second distance d2 in the first direction away from the first arm 112a, and the first distance d1 is greater than the second distance d2.

The pair of prongs are deformable, and once the pair of prongs pass through the opening, the pair of prongs revert to their original configuration, locking the male locking member 150 within the female locking member 152. The male and female locking members 150, 152 are specifically configured so that the male and female locking members 150 and 152 engage one another only when the pair of clip arms 112 are drawn toward one another beyond a predetermined threshold distance. Thus, the pair of clip arms 112 may be moved between the tissue receiving and tissue gripping configurations multiple times, as desired, prior to locking of the clip unit 102 in the tissue gripping configuration.

Although the clip unit 102 is described as including the above locking mechanisms 150 and 152, it will be understood by those of skill in the art that a clip unit of the present disclosure may include any of a variety of corresponding mating features for locking the clip arms relative to one another.

The clip unit 102 further includes a restraining mechanism which is operated associated with the locking mechanisms and configured to prevent the target tissue from being pinched between the locking mechanisms when the clip unit 102 is drawn into the sheath 108 to close the pair of clip arms 112 toward the closed tissue gripping configuration. As will be described in details below, the restraining mechanism may have different configurations and may be disposed with different position relationships with respect to the locking mechanisms, as long as the restraining mechanism is configured to be suitable to prevent the target tissue to be pinched between the locking mechanisms.

First Embodiment

FIG. 8A schematically illustrates a clip unit in a first configuration in which a pair of clip arms are opened to receive a target tissue according to a first exemplary embodiment, and FIG. 8B is a cross-sectional view taken line A-A of FIG. 8A. In the first exemplary embodiment, the clip unit 102 includes a restraining mechanism mounted on the pair of clip arms 112. Specifically, the restraining mechanism includes a first restraining member 181 and a second restraining member 182. The first restraining member 181 is disposed on and extends from an inner surface of a first one of the clip arms 112 toward a second one of the clip arms 112. The second restraining member 182 is disposed on and extend from an inner surface of the second one of the clip arms 112 toward the first one of the clip arms 112. The restraining first and second members 181 and 182 may be located more distally than the locking members 150 and 152, respectively. Alternatively, the restraining members 181 and 182 may be attached to the distal end sides of the locking members 150 and 152, respectively.

Figure 8D:
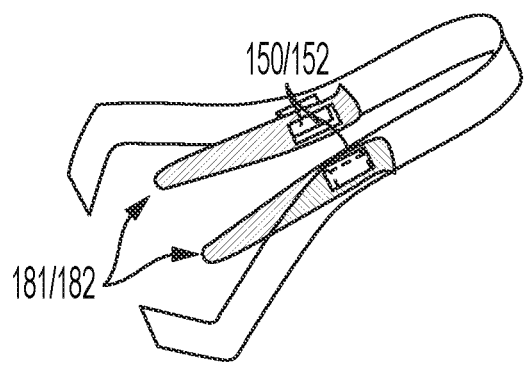
FIG. 8D is a perspective view schematically illustrating an exemplary structural arrangement between restraining members and locking members.
Figure 8E:
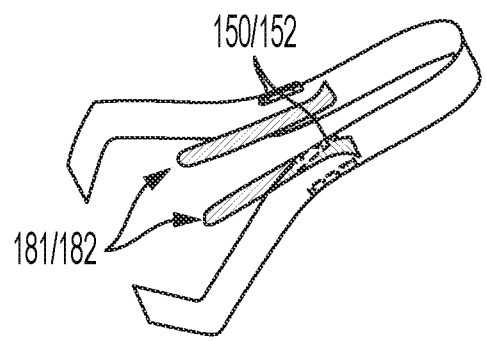
FIG. 8E is a perspective view schematically illustrating another exemplary structural arrangement between restraining members and locking members.

Moreover, as shown in FIG. 8C, the first restraining member 181 and the second restraining member 182 may be respectively located on the pair of clip arms 112 more proximally than the locking members 150 and 152. In this situation, a distal end portion of the first restraining member 181a and a distal end portion of the second restraining member 182a should be positioned more distally than the locking members 150 and 152, respectively. FIG. 8D is a perspective view schematically illustrating an exemplary structural arrangement between the restraining members 181 and 182 and the locking members 150 and 152. As shown in FIG. 8D, each of the restraining members 181 and 182 may include an opening that is sized and shaped for a corresponding one of the locking members 150 and 152 to extend from the inner surface of one of the clip arms 112 through the opening without interfering with the corresponding one of the restraining members 181 and 182. FIG. 8E is a perspective view schematically illustrating another exemplary structural arrangement between the restraining members 181 and 182 and the locking members 150 and 152. As shown in FIG. 8E, the locking members 150 and 152 may be each attached to two sides of the respective clip arms 112 so that the restraining members 181 and 182 each extend passing through the respective locking members 150 and 152 in a distal direction without interfering with the respective locking members 150 and 152.

As described above, when the clip unit 102 is in the first configuration, the pair of clip arms 112 are opened to receive the target tissue 200. As will be described in detail below, the first and second restraining members 181 and 182 are sized and shaped to prevent the target tissue 200 from being pinched between the locking mechanisms 150 and 152 when the pair of clip arms 112 are moved to close and grip the target tissue 200.

In this exemplary embodiment, the first and second restraining members 181 and 182 are each configured as a curved bar, which may have a flat/round front end surface that comes to contact with the target tissue 200 without hurting the target tissue 200, when the pair of clip arms 112 are moved to receive and grip the target tissue 200. The invention is not limited to the flat/round shape for the front end surface. The front end surface of each of the restraining members 181 and 182 may have any suitable protection shape that can minimize or prevent the restraining member 181 and 182 from causing unwanted damage to the target tissue 200. Additionally, when the restraining members 181 and 182 are configured as a curved bar, the curvature can be such that the distal ends of the restraining members (i.e., the end not attached to the clip arms 181, 182) can be toward the distal end of the clip unit 102 (i.e., toward the opening through which the target tissue 200 is received by the clip unit 102) or can be toward the proximal end of the clip unit 102 (i.e., toward proximal end 114 connected to a connector 116).

The first and second restraining members 181 and 182 may be formed of the same single piece of material that is employed to form the pair of clip arms 112 as noted above. Alternatively, the pair of restraining members 181 and 182 may be formed of a different material from the pair of clip arms 112 and thus are attached to the pair of clip arms 112 during an assembly process by an adhesive substance or soldering.

The first and second restraining members 181 and 182 may be made of any suitable biocompatible materials, such as, but not limited to, polymeric polymers and materials, including fillers such as metals, carbon fibers, glass fibers or ceramics, and combinations thereof. The metals may include cobalt chrome alloy, nickel titanium alloy, titanium, stainless steel, and the like. Useful, but non-limiting, polymeric materials include polyethylene, polypropylene, polyvinyl chloride, polytetrafluoroethylene, fluorinated ethylene propylene copolymer, polyvinyl acetate, polystyrene, polyethylene terephthalate), naphthalene dicarboxylate derivatives, such as polyethylene naphthalate, polybutylene naphthalate, polytrimethylene naphthalate and trimethylenediol naphthalate, polyurethane, polyurea, silicone rubbers, polyamides, polycarbonates, polyaldehydes, natural rubbers, polyester copolymers, styrene-butadiene copolymers, polyethers, fully or partially halogenated polyethers, polyamide/ polyether polyesters, and copolymers and combinations thereof, and ABS (acrylonitrile butadiene styrene copolymer), PEEK (Poly Ether Ether Ketone), etc.

Figure 9A:
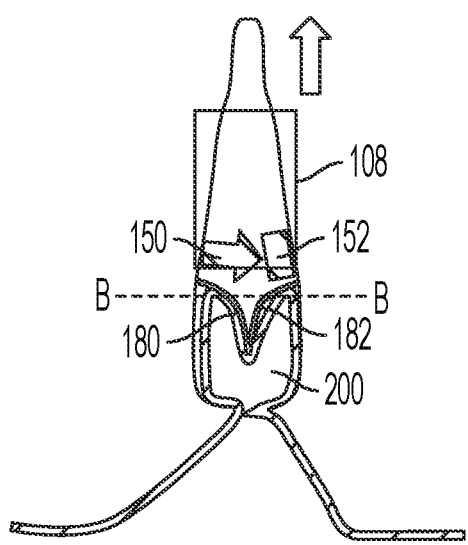
FIG. 9A is a front view schematically illustrating a clip unit in a second configuration in which the target tissue is gripped by the pair of clip arms are according to an exemplary embodiment.
Figure 9B:
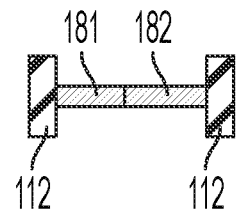
FIG. 9B is a magnified cross-sectional view taken line B-B of FIG. 9A.

FIG. 9A is a front view schematically illustrating a clip unit in a second configuration in which the target tissue is gripped by the pair of clip arms are according to the first exemplary embodiment, and FIG. 9B is a cross-sectional view taken line B-B of FIG. 9A. Once the target tissue 200 is received between the clip arms 112 as shown in FIG. 8A, the clip assembly 102 is moved toward the second configurator, in which the target tissue 200 is gripped by the pair of clip arms 112, by moving the control member 110 proximally relative to the clip assembly 102. With the pair of clip arms 112 are closed to each other, the first and second restraining members 181 and 182 are moved to contact each other and are deformed to extend distally, thereby pushing the target tissue away from the locking mechanisms 150 and 152. As shown in FIG. 93, the restraining members 181 and 182 contact each other and form a stopping bar in front of the locking mechanisms 150 and 152. The stopping bar formed by the restraining members 181 and 182 is able to stop die target tissue 200 from entering into an area between the locking mechanisms 150 and 150, thereby preventing the target tissue 200 from being pinched therebetween.

Also, the restraining members 181 and 182 may be made flexible and deformable (i.e., movable toward one another). When the pair of clip arms 112 are closed further to each other, as shown in FIG. 9A, the stopping bar formed by the restraining members 181 and 182 is moved further distally to keep the target tissue away from the locking mechanisms 150 and 152.

When it is confirmed that a desired portion of the target tissue 200 is gripped between the clip arms 112 (e.g., portions of tissue on opposite sides of a bleeding wound), the control member 110 is drawn further proximally relative to the clip assembly 102 (via the spool 124) to lock the clip assembly 102 in the closed configuration. That is, the clip arms 112 are drawn further proximally into the sleeve 1088 until the locking mechanisms 150, 152 engage one another, locking the clip arms 112 relative to one another.

FIG. 10A is a front view schematically illustrating a clip unit in a first configuration in which a pair of clip arms are opened to receive a target tissue according to another exemplary embodiment, and FIG. 10B is a cross-sectional view taken line C-C of FIG. 10A. FIG. 11A is a front view schematically illustrating a clip unit in a second configuration in which the target tissue is gripped by the pair of clip arms are according to another exemplary embodiment, and FIG. 11B is a cross-sectional view taken line D-D of FIG. 11A.

In this modified exemplary embodiment, as shown in FIG. 10B, the restraining member 181 is disposed on the first one of the clip arms 112 at a position different from a position where the restraining member 182 is disposed on the second one of the clip arms 112. Thus, the restraining members 182 and 182 do not contact each other even when the clip unit 102 is drawn toward the second configuration in which the pair of clip arms 112 are closed to grip the target tissue 200. As shown in FIGS. 11A and 111B, the restraining member 181 and 182 cross each other in the second configuration, in which each of the restraining member 181 and 182 serves as a stopping bar (anti-intrusion mechanism) to prevent the target tissue 200 from being pinched between the locking mechanisms 150 and 152 when the locking mechanisms 150 and 152 are moved to engage one another.

Figure 12A:
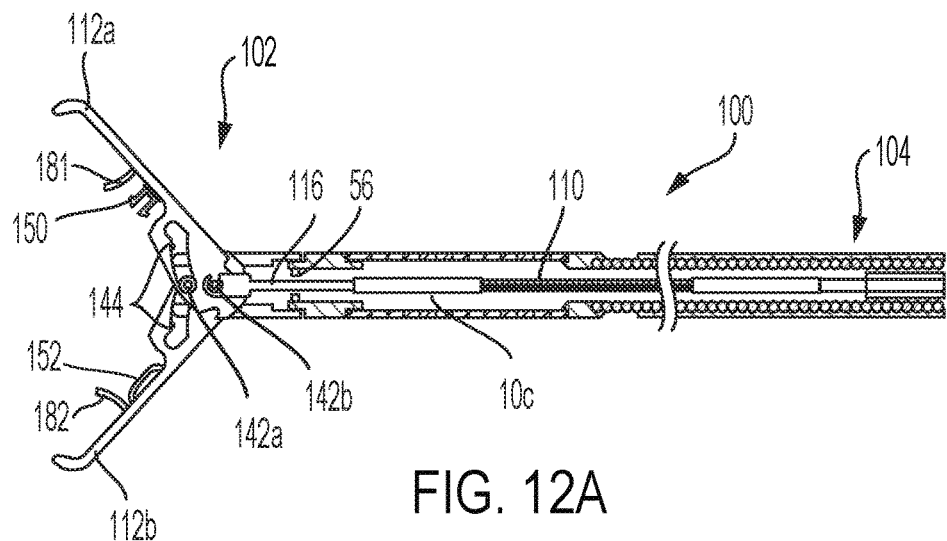
FIGS. 12A-12B show side views of distal portions of additional exemplary embodiments of a clip device system related to the first embodiment.
Figure 12B:
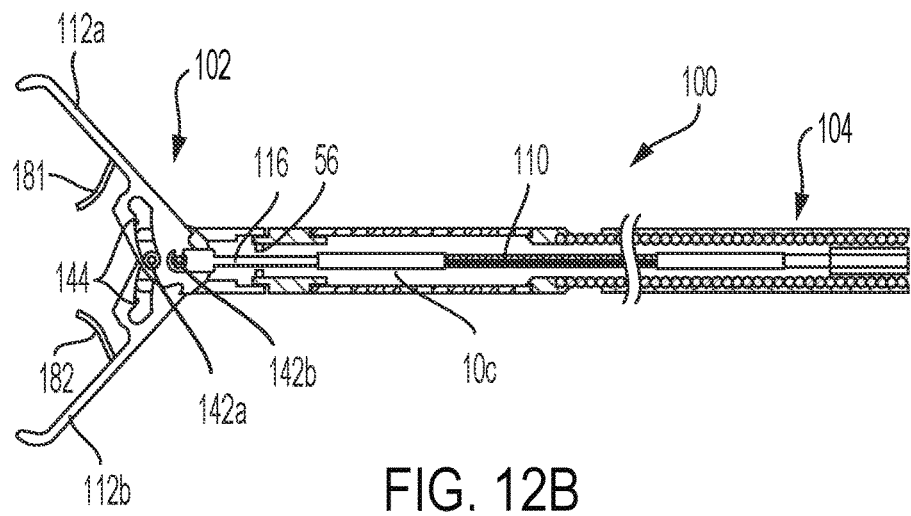

FIGS. 12A and 12B show side views of a distal portion of additional exemplary embodiments of a clip device system related to the first embodiment. The clip delivery system 100 includes a clip unit 102 attached to distal end of an applicator 104. For example, clip unit 102 can be connected to a control member 110 via a connector 116. The control member 110 is movable within a plenum of the applicator 104 and manipulation of the control member 110, e.g., retracting and extending, moves the clip unit 102 to be withdrawn into at least a portion of the passage 10c or extended out from an opening at the distal end of the control member 110. Stop 56 serves to delimit the distance the clip unit 102 can move in the retracting direction.

As shown in FIGS. 12A and 12B, the clip unit 102 has two clip arms 112a, 112b and the bases of the two clip arms 112a, 112b are pivotable relative to each other about pivot connection 142a. In the embodiment shown, a groove or track 144 in the clip arms 112a, 112b accommodates the movement of the clip arms 112a, 112b as they move from the open position, i.e., the first configuration, to the closed position, i.e., the second configuration. Additionally, the clip unit 102 is pivotable and/or rotatable relative to the control member 110 about pivot connection 142b.

As with other embodiments disclosed herein, each clip arm 112a, 112b includes locking mechanisms to lock the pair of clip arms when the clip unit 102 is in the closed tissue gripping configuration and the locking mechanisms includes corresponding mating features 150, 152 (e.g., a pair of locking members—male lock feature 150 and female lock feature 15) for locking the clip arms 112 in the closed tissue gripping configuration. As with other embodiments disclosed herein, each clip arm 112a, 112b also includes a restraining mechanism mounted on the pair of clip arms 112a, 112b. Specifically, the restraining mechanism includes a first restraining member 181 and a second restraining member 182. Any of the embodiments disclosed herein for the locking mechanisms and restraining mechanism can be utilized in the clip unit 102 of the embodiment shown and described with respect to FIGS. 12A and 12B. In some embodiments, the clip unit 102 only includes a restraining mechanism (such as first restraining member 181 and second restraining member 182 as shown in FIG. 12B), which function to suppress tissue from entering the proximal side of the clip unit 102 and interfering with the pivoting of the clip unit 102. In other respects, such as other structural features, configuration and operation, the embodiments of the clip unit 102 and clip arms 112a, 112b in FIGS. 12A and 12B can be consistent with the structural features, configuration and operation for the first embodiments describe above with reference to FIGS. 2 to 11.

Second Embodiment

Figure 13A:
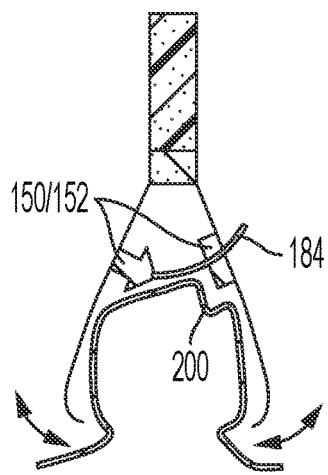
FIG. 13A is a front view schematically illustrating a clip unit in a first configuration in which a pair of clip arms are opened to receive a target tissue according to a further exemplary embodiment.
Figure 13B:
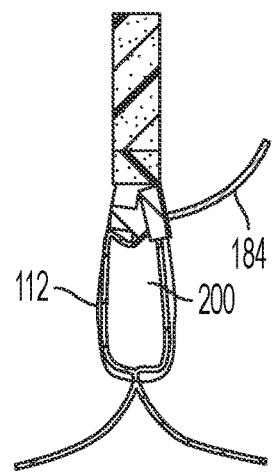
FIG. 13B is a front view schematically illustrating a clip unit in a second configuration in which the pair of clip arms are closed and grip the target tissue.

FIG. 13A is a front view schematically illustrating a clip unit in a first configuration in which a pair of clip arms are opened to receive a target tissue according to a second exemplary embodiment, and FIG. 13B is a front view schematically illustrating a clip unit in a second configuration in which the pair of clip arms are closed and grip the target tissue according to the second exemplary embodiment.

In the second exemplary embodiment, the restraining mechanism is a restraining rail 184 that connects the locking mechanism 150 to the locking mechanism 152. The restraining rail 184 may be shaped as a bar and serves as a stopping bar between the locking mechanisms 150 and 152. The restraining rail 184 is able to stop the target tissue 200 from entering into an area between the locking mechanisms 150 and 152, thereby preventing the target tissue 200 from being pinched therebetween.

As shown in FIG. 13A, the clip unit 102 includes the restraining rail 184, which has one end attached to a tip end of the locking mechanism 150, and the other end passing through a through-hole (or slot) formed on the locking mechanism 152. By this exemplary configuration, the restraining rail 184 serves as a stopping bar that is able to stop the target tissue 200 from entering into an area between the locking mechanisms 150 and 152, thereby preventing the target tissue 200 from being pinched therebetween.

The one end of the restraining rail 184 may be bonded to the tip of the locking mechanism 150 by an adhesive substance, heating or pressing process. The through-hole may be part of an opening of the locking mechanism 152, which is sized and shaped to permit the locking mechanism 150 to be received therein and also to permit the restraining rail 184 to be passed therethrough.

As shown in FIG. 13B, when the clip unit 102 is drawn proximally toward the second configuration, in which the pair of clip arms 112 are closed to grip the target tissue 200, the restraining rail 184 passes through the opening of the locking mechanism 152, during which the target tissue 200 is prevented from being pinched by the locking mechanisms 150 and 152 by the restraining rail 184. Once the locking mechanisms 150 and 152 are engaged to one another, the restraining rail 184 is moved outside the clip unit 102.

The restraining rail 184 is made of a flexible and deformable material, and may be formed of any suitable biocompatible materials, such as, but not limited to, polymeric polymers and materials, including fillers such as metals, carbon fibers, glass fibers or ceramics, and combinations thereof. The metals may include cobalt chrome alloy, nickel titanium alloy, titanium, stainless steel, and the like. Useful, but non-limiting, polymeric materials include polyethylene, polypropylene, polyvinyl chloride, polytetrafluoroethylene, fluorinated ethylene propylene copolymer, polyvinyl acetate, polystyrene, polyethylene terephthalate), naphthalene dicarboxylate derivatives, such as polyethylene naphthalate, polybutylene naphthalate, polytrimethylene naphthalate and trimethylenediol naphthalate, polyurethane, polyurea, silicone rubbers, polyamides, polycarbonates, polyaldehydes, natural rubbers, polyester copolymers, styrene-butadiene copolymers, polyethers, fully or partially halogenated polyethers, polyamide/polyether polyesters, and copolymers and combinations thereof, and ABS (acrylonitrile butadiene styrene copolymer), PEEK (Poly Ether Ether Ketone), etc.

Figure 14A:
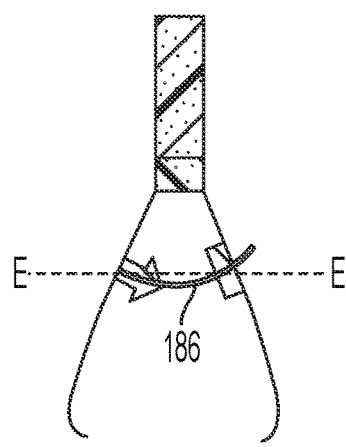
FIG. 14A is a front view schematically illustrating a clip unit in a first configuration in which a pair of clip arms are opened to receive a target tissue according to another exemplary embodiment.
Figure 14B:
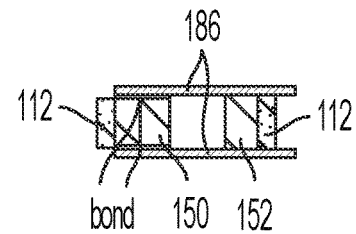
FIG. 14B is a magnified cross-sectional view taken line E-E of FIG. 14A.

FIG. 14A is a front view schematically illustrating a clip unit in a first configuration in which a pair of clip arms are opened to receive a target tissue according to another exemplary embodiment, and FIG. 14B is a cross-sectional view taken line E-E of FIG. 14A.

In this modified exemplary embodiment, as shown in FIGS. 14A and 14B, a pair of restraining rails 186 each have one end attached to a corresponding side of the locking mechanism 150, and the other end passing through a corresponding through-hole of the locking mechanism 152. Or the other end of each of the pair of restraining rails 186 may pass through a groove formed on a corresponding side of the locking mechanism 152 and the second one of the pair of clip arms 112.

The one end of each of the restraining rails 186 may be bonded to the corresponding side of the locking mechanism 150 by an adhesive substance, heating or pressing process. The corresponding through-hole may be part of an opening of the locking mechanism 152, which is sized and shaped to permit the locking mechanism 150 to be received therein and also to permit the restraining rails 186 to be passed therethrough. Or, the groove is sized and shaped to permit the restraining rails 186 to be passed through the locking mechanism 152 and the second one of the pair of clip arms 112.

The invention is not limited to have the pair of restraining rails 186. The invention may have one single restraining rail 186, which has its one end attached to one side of the locking mechanism 150, and its other end passing through a through-hole of the locking mechanism 152. Or the other end of the single restraining rail 186 may pass through a groove formed on one side of the locking mechanism 152 and the second one of the pair of clip arms 112.

The restraining rails 186 may be made of a flexible and deformable material, and may be formed of any suitable biocompatible materials, such as, but not limited to, polymeric polymers and materials, including fillers such as metals, carbon fibers, glass fibers or ceramics, and combinations thereof. The metals may include cobalt chrome alloy, nickel titanium alloy, titanium, stainless steel, and the like. Useful, but non-limiting, polymeric materials include polyethylene, polypropylene, polyvinyl chloride, polytetrafluoroethylene, fluorinated ethylene propylene copolymer, polyvinyl acetate, polystyrene, polyethylene terephthalate), naphthalene dicarboxylate derivatives, such as polyethylene naphthalate, polybutylene naphthalate, polytrimethylene naphthalate and trimethylenediol naphthalate, polyurethane, polyurea, silicone rubbers, polyamides, polycarbonates, polyaldehydes, natural rubbers, polyester copolymers, styrene-butadiene copolymers, polyethers, fully or partially halogenated polyethers, polyamide/polyether polyesters, and copolymers and combinations thereof, and ABS (acrylonitrile butadiene styrene copolymer), PEEK (Poly Ether Ether Ketone), etc.

Figure 15A:
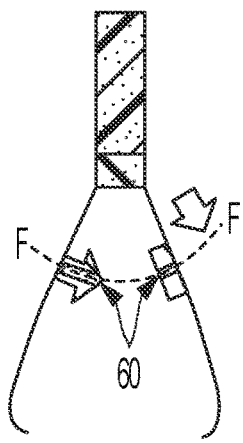
FIG. 15A is a front view schematically illustrating a clip unit in a first configuration in which a pair of clip arms are opened to receive a target tissue according to another exemplary embodiment.
Figure 15B:
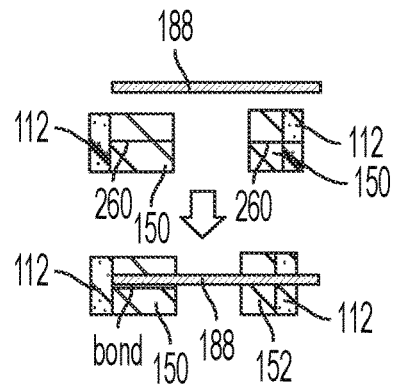
FIG. 15B is a magnified cross-sectional view taken line F-F of FIG. 15A.

FIG. 15A is a front view schematically illustrating a clip unit in a first configuration in which a pair of clip arms are opened to receive a target tissue according to another exemplary embodiment, and FIG. 15B is a cross-sectional view taken line E-E of FIG. 15A.

In this modified exemplary embodiment, as shown in FIGS. 15A and 15B, a groove 260 is formed at one side of each of the locking mechanisms 150 and 152, and a restraining rail 188 has one end attached to the groove 260 of the one locking mechanism 150, and the other end passing through the groove 260 of the other locking mechanism 152.

The one end of the restraining rail 188 may be bonded to the groove 260 of the locking mechanism 150 by an adhesive substance, heating or pressing process. The groove 260 is sized and shaped to permit the restraining rail 188 to be passed through the locking mechanism 152 and the second one of the pair of clip arms 112.

The restraining rail 188 may be made of a flexible and deformable material, and may be formed of any suitable biocompatible materials, such as, but not limited to, polymeric polymers and materials, including fillers such as metals, carbon fibers, glass fibers or ceramics, and combinations thereof. The metals may include cobalt chrome alloy, nickel titanium alloy, titanium, stainless steel, and the like. Useful, but non-limiting, polymeric materials include polyethylene, polypropylene, polyvinyl chloride, polytetrafluoroethylene, fluorinated ethylene propylene copolymer, polyvinyl acetate, polystyrene, polyethylene terephthalate), naphthalene dicarboxylate derivatives, such as polyethylene naphthalate, polybutylene naphthalate, polytrimethylene naphthalate and trimethylenediol naphthalate, polyurethane, polyurea, silicone rubbers, polyamides, polycarbonates, polyaldehydes, natural rubbers, polyester copolymers, styrene-butadiene copolymers, polyethers, fully or partially halogenated polyethers, polyamide/polyether polyesters, and copolymers and combinations thereof, and ABS (acrylonitrile butadiene styrene copolymer), PEEK (Poly Ether Ether Ketone), etc.

Figure 16:
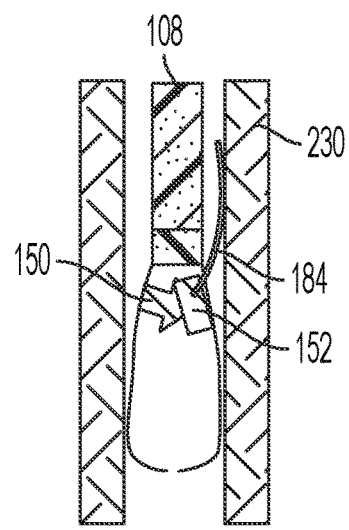
FIG. 16 is a view schematically illustrating a clip unit with a restraining rail that is inserted into a channel of an endoscope according to an exemplary embodiment.
Figure 17:
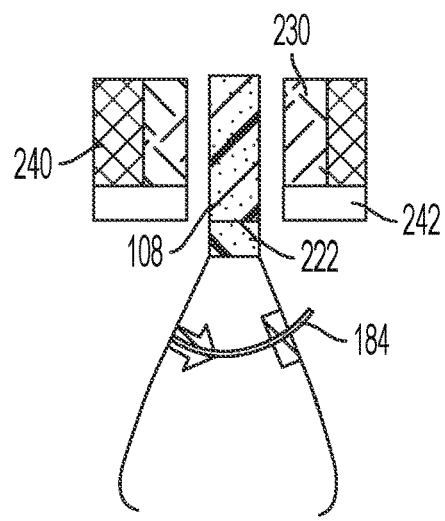
FIG. 17 a view schematically illustrating a clip unit with a restraining rail that is in a first configuration according to an exemplary embodiment.

FIG. 16 is a view schematically illustrating a clip unit with a restraining rail that is inserted into a channel of an endoscope according to an exemplary embodiment, and FIG. 17 a view schematically illustrating a clip unit with a restraining rail that is in a first configuration according to an exemplary embodiment. As shown in FIGS. 16 and 17, in use, after the clip unit 102 has been loaded onto the applicator 104, the clip unit 102 in a closed configuration is disposed at the distal end of the sheath 108 and the pair of clip arms 112 projecting out of an open end 222 of the sheath 108 are closed. In this configuration, the clip unit 102 is inserted through a channel 230 of an insertion portion 240 of an endoscope (or any other insertion device) and inserted into the body (e.g., through a natural body lumen) to a site adjacent to a target portion of tissue to be clipped. The restraining rail 184 is connected to the locking mechanisms 150 and 152, and is deformed to be disposed between the clip unit 102 and an inner surface of the channel 230. Once the insertion portion 240 arrives the side adjacent to the target portion to be clipped, the clip unit 102 is pushed out of a channel 230 through an endoscope tip 242, and the pair of clip arms 112 are opened for use.

Figure 18:
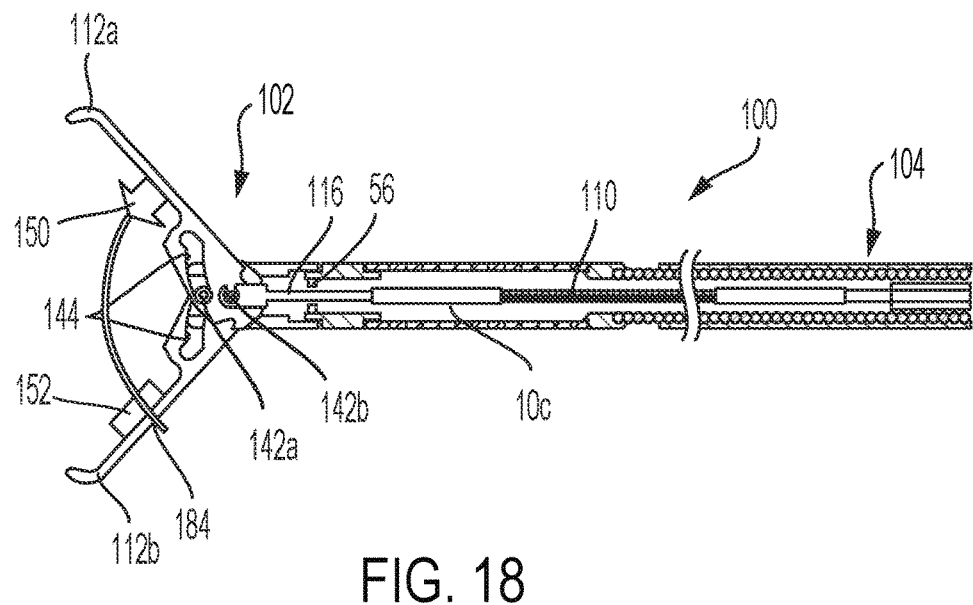
FIG. 18 shows a side view of a distal portion of an additional exemplary embodiment of a clip device system related to the second embodiment.

FIG. 18 shows a side view of a distal portion of an additional exemplary embodiment of a clip device system related to the second embodiment. The clip delivery system 100 includes a clip unit 102 attached to distal end of an applicator 104. For example, clip unit 102 can be connected to a control member 110 via a connector 116. The control member 110 is movable within a plenum of the applicator 104 and manipulation of the control member 110, e.g., retracting and extending, moves the clip unit 102 to be withdrawn into at least a portion of the passage 10c or extended out from an opening at the distal end of the control member 110. Stop 56 serves to delimit the distance the clip unit 102 can move in the retracting direction.

As shown in FIG. 18, the clip unit 102 has two clip arms 112a, 112b and the bases of the two clip arms 112a, 112b are pivotable relative to each other about pivot connection 142a.

In the embodiment shown, a groove or track 144 in the clip arms 112a, 112b accommodates the movement of the clip arms 112a, 112b as they move from the open position, i.e., the first configuration, to the closed position, i.e., the second configuration. Additionally, the clip unit 102 is pivotable and/or rotatable relative to the control member 110 about pivot connection 142b.

As with other embodiments disclosed herein, each clip arm 112a, 112b includes locking mechanisms to lock the pair of clip arms when the clip unit 102 is in the closed tissue gripping configuration and the locking mechanisms includes corresponding mating features 150, 152 (e.g., a pair of locking members—male lock feature 150 and female lock feature 15) for locking the clip arms 112 in the closed tissue gripping configuration. As with other embodiments disclosed herein, one of the clip arms 112a, 112b also includes a restraining mechanism mounted thereon. Specifically, the restraining mechanism includes restraining rail 184. Any of the embodiments disclosed herein for the locking mechanisms and restraining mechanism can be utilized in the clip unit 102 of the embodiment shown and described with respect to FIG. 18. In some embodiments, the clip unit 102 includes a restraining mechanism (such as restraining rail 184 as shown in FIGS. 13A-B, 14A-B and 16-17 or restraining rail 188 as shown in FIGS. 15A-B). In other respects, such as other structural features, configuration and operation, the embodiments of the clip unit 102 and clip arms 112a, 112b in FIG. 18 can be consistent with the structural features, configuration and operation for the second embodiments describe above with reference to FIGS. 13A-B to 17.

Third Embodiment

Figure 19A:
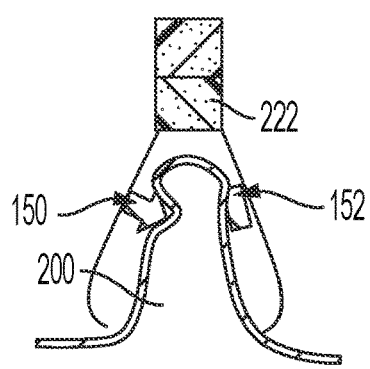
FIG. 19A is a front view schematically illustrating a clip unit in a first configuration in which a pair of clip arms are opened to receive a target tissue according to an exemplary embodiment.
Figure 19B:
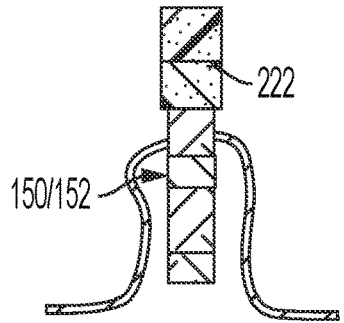
FIG. 19B is a side view schematically illustrating the clip unit of FIG. 19A.
Figure 19C:
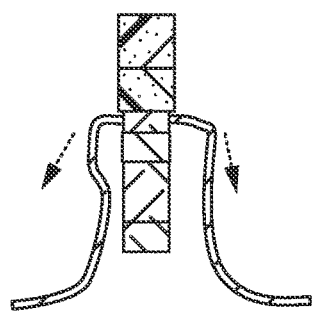
FIG. 19C is a side view schematically illustrating the clip unit of FIG. 19A when the clip unit is drawn into a sheath toward a second configuration.
Figure 19D:
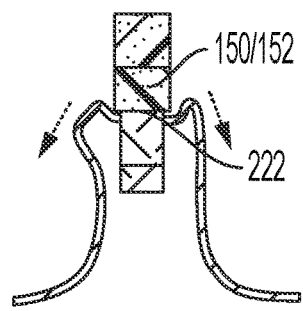
FIG. 19D is a side view schematically illustrating the clip unit of FIG. 19A when the clip unit is the second configuration.

FIG. 19A is a front view schematically illustrating a clip unit in a first configuration in which a pair of clip arms are opened to receive a target tissue according to a third exemplary embodiment, FIG. 19B is a side view schematically illustrating the clip unit of FIG. 19A, FIG. 19C is a side view schematically illustrating the clip unit of FIG. 19A when the clip unit is drawn into a sheath toward a second configuration, and FIG. 19D is a side view schematically illustrating the clip unit of FIG. 19A when the clip unit is the second configuration.

In the third exemplary embodiment, the positions of the locking mechanisms 150 and 152 are adjusted such that the locking mechanisms 150 and 152 are disposed more proximally than those in the first and second exemplary embodiments, so that the locking mechanism 150 and 152 are engaged to one another inside the sheath 108. By this adjustment, the open end 222 of the sheath 108 can serve the restraining mechanism, because the open end is sized and shaped such that the target tissue 200 cannot enter into the sheath 108 through the opening, thereby preventing the target tissue 200 from being pinched between the locking mechanisms 150 and 152.

As shown in FIGS. 19A-19D, when the clip unit 102 is drawn proximally into the sheath 108, the pair of clip arms 112 are moved toward the closed configuration. Even if there is a portion of the target tissue 200 that projects in-between the locking mechanisms 150 and 152, since the locking mechanisms 150 and 152 are adjusted to engage one another inside the sheath 108, the portion of the target tissue 200 is blocked outside the sheath 108 by the open end 222.

Figure 20A:
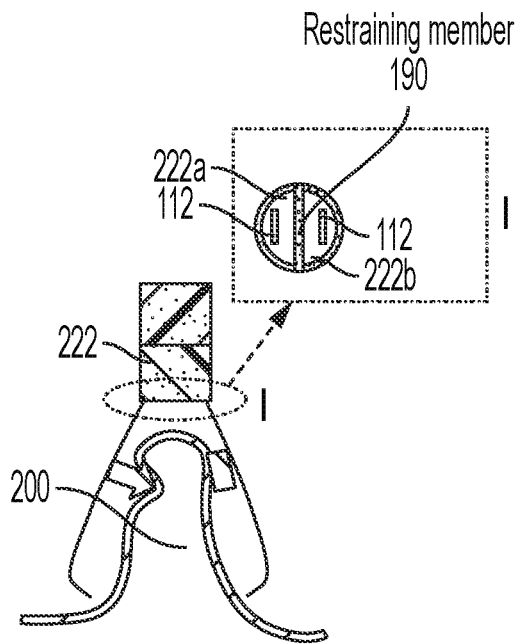
FIG. 20A is a front view schematically illustrating a clip unit in a first configuration in which a pair of clip arms are opened to receive a target tissue according to one exemplary embodiment.
Figure 20B:
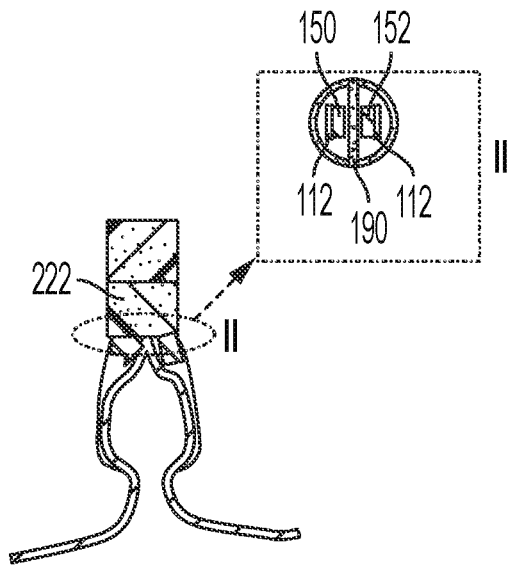
FIG. 20B is a front view schematically illustrating a clip unit in a second configuration in which a pair of clip arms are closed to grip the target tissue.

FIG. 20A is a front view schematically illustrating a clip unit in a first configuration in which a pair of clip arms are opened to receive a target tissue according to another exemplary embodiment, and FIG. 20B is a front view schematically illustrating a clip unit in a second configuration in which a pair of clip arms are closed to grip the target tissue.

As shown in FIGS. 20A and 20B, the open end 222 of the sheath 108 includes a restraining member 190 (see the boxes I in FIG. 20A and II in FIG. 20B) that is a partition member equally dividing the open end 222 into a first opening 222a for the first one of the pair of clip arms 112 and a second opening 222b for the second one of the pair of clip arms 112. The first opening 222a is sized and shaped to permit the first one of the pair of clip arms 112 and the locking mechanism 150 to pass through, and the second opening 222b is sized and shaped to permit the second one of the pair of clip arms 112 and the locking mechanism 152 to pass through. By this configuration, even if there is a portion of the target tissue 200 that projects in-between the locking mechanisms 150 and 152, since the locking mechanisms 150 and 152 are adjusted to engage one another inside the sheath 108, the portion of the target tissue 200 is blocked outside the sheath 108 by the restraining member 190.

Figure 20C:
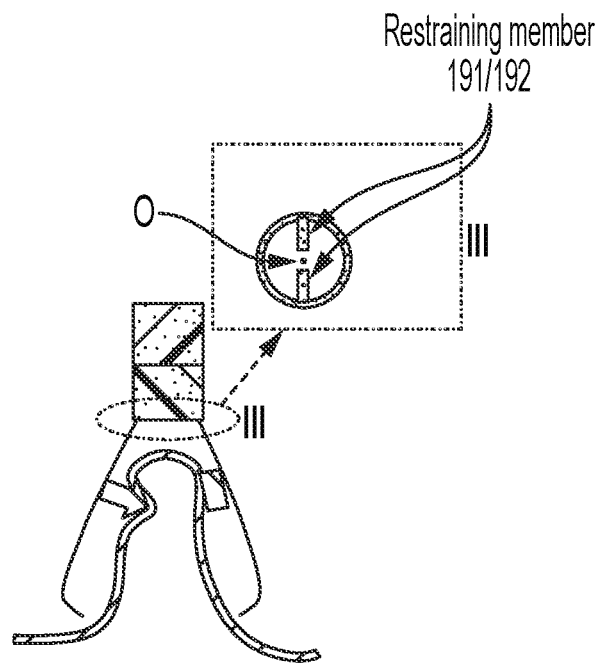
FIG. 20C is a front view schematically illustrating a clip unit in the first configuration according to another exemplary embodiment that is different from the one in FIG. 20A.

FIG. 20C is a front view schematically illustrating a clip unit in the first configuration according to a modified embodiment of FIG. 20A. As shown in FIG. 20C, the open end 222 of the sheath 108 includes two restraining members 191 and 192 (see the boxes III in FIG. 20C). The restraining member 191 is a bar-shaped member that extends inwardly from the open end 222 toward a center axis "O" of the open end 222. The restraining member 192 is also a bar-shaped member that extends inwardly from the open end 222 and faces the restraining member 191 without contacting the restraining member 191. By this configuration, even if there is a portion of the target tissue 200 that projects in-between the locking mechanisms 150 and 152, since the locking mechanisms 150 and 152 are adjusted to engage one another inside the sheath 108, the portion of the target tissue 200 can be blocked outside the sheath 108 by the restraining members 190 and 191.

The restraining member 190 may be integrally formed with the sheath 108, or may be bonded to the open end 222 by an adhesive substance, heating or pressing process. The restraining members 191 and 192 may also be formed integrally with the sheath 108, or be respectively attached to an inner surface of the open end 222 by an adhesive substance, heating or pressing process.

The restraining member 190 may be made of any suitable biocompatible materials, such as, but not limited to, polymeric polymers and materials, including fillers such as metals, carbon fibers, glass fibers or ceramics, and combinations thereof. The metals may include cobalt chrome alloy, nickel titanium alloy, titanium, stainless steel, and the like. Useful, but non-limiting, polymeric materials include polyethylene, polypropylene, polyvinyl chloride, polytetrafluoroethylene, fluorinated ethylene propylene copolymer, polyvinyl acetate, polystyrene, polyethylene terephthalate), naphthalene dicarboxylate derivatives, such as polyethylene naphthalate, polybutylene naphthalate, polytrimethylene naphthalate and trimethylenediol naphthalate, polyurethane, polyurea, silicone rubbers, polyamides, polycarbonates, polyaldehydes, natural rubbers, polyester copolymers, styrene-butadiene copolymers, polyethers, fully or partially halogenated polyethers, polyamide/polyether polyesters, and copolymers and combinations thereof, and ABS (acrylonitrile butadiene styrene copolymer), PEEK (Poly Ether Ether Ketone), etc.

Figure 21:
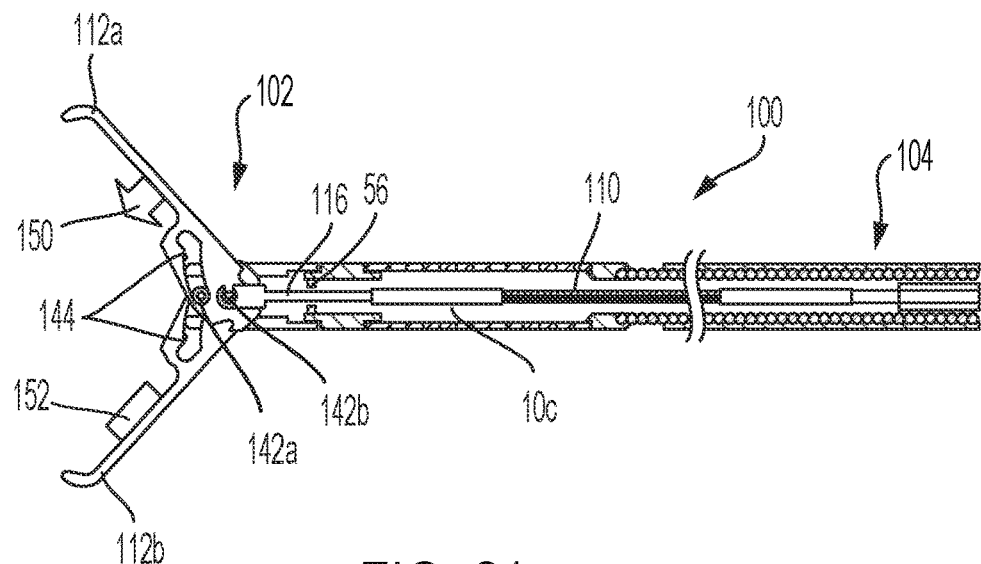
FIG. 21 shows a side view of a distal portion of an additional exemplary embodiment of a clip device system related to the third embodiment.

FIG. 21 shows a side view of a distal portion of an additional exemplary embodiment of a clip device system related to the third embodiment. The clip delivery system 100 includes a clip unit 102 attached to distal end of an applicator 104. For example, clip unit 102 can be connected to a control member 110 via a connector 116. The control member 110 is movable within a plenum of the applicator 104 and manipulation of the control member 110, e.g., retracting and extending, moves the clip unit 102 to be withdrawn into at least a portion of the passage 10c or extended out from an opening at the distal end of the control member 110. Stop 56 serves to delimit the distance the clip unit 102 can move in the retracting direction.

As shown in FIG. 21, the clip unit 102 has two clip arms 112a, 112b and the bases of the two clip arms 112a, 112b are pivotable relative to each other about pivot connection 142a. In the embodiment shown, a groove or track 144 in the clip arms 112a, 112b accommodates the movement of the clip arms 112a, 112b as they move from the open position, i.e., the first configuration, to the closed position, i.e., the second configuration. Additionally, the clip unit 102 is pivotable and/or rotatable relative to the control member 110 about pivot connection 142b.

As with other embodiments disclosed herein, each clip arm 112a, 112b includes locking mechanisms to lock the pair of clip arms when the clip unit 102 is in the closed tissue gripping configuration and the locking mechanisms includes corresponding mating features 150, 152 (e.g., a pair of locking members—male lock feature 150 and female lock feature 15) for locking the clip arms 112 in the closed tissue gripping configuration. Any of the embodiments disclosed herein for the locking mechanisms can be utilized in the clip unit 102 of the embodiment shown and described with respect to FIG. 21. In some embodiments, the clip unit 102 includes a locking mechanism as shown in FIGS. 19A-D and 20A-B and does not include a retaining mechanism. In other respects, such as other structural features, configuration and operation, the embodiments of the clip unit 102 and clip arms 112a, 112b in FIG. 18 can be consistent with the structural features, configuration and operation for the third embodiments describe above with reference to FIGS. 19A-D and 20A-B.

Fourth Embodiment

Figure 22A:
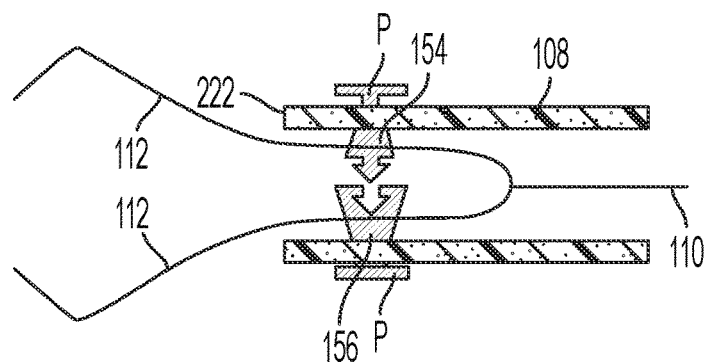
FIG. 22A is a side view schematically illustrating a clip unit in a first configuration in which a pair of clip arms are opened according to a still further exemplary embodiment.
Figure 22B:
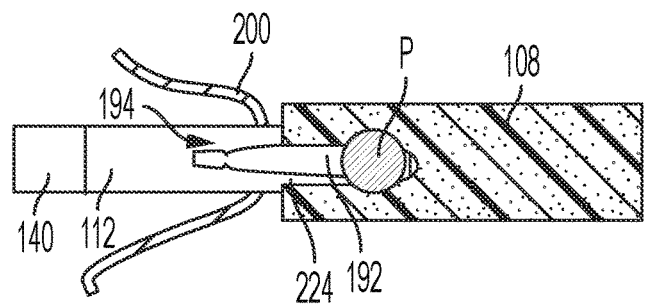
FIG. 22B is a top view schematically illustrating the clip unit of FIG. 22A.
Figure 22C:
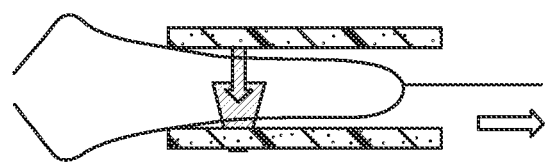
FIG. 22C is a side view schematically illustrating the clip unit in a second configuration in which the pair of clip arms are closed.
Figure 22D:
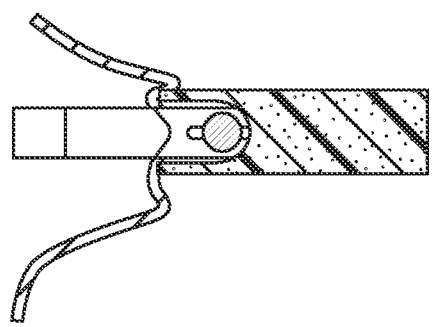
FIG. 22D is a top view schematically illustrating the clip unit of FIG. 22C.

FIG. 22A is a side view schematically illustrating a clip unit in a first configuration in which a pair of clip arms are opened according to a fourth exemplary embodiment, FIG. 22B is a top view schematically illustrating the clip unit of FIG. 22A, FIG. 22C is a side view schematically illustrating the clip unit in a second configuration in which the pair of clip arms are closed, and FIG. 22D is a top view schematically illustrating the clip unit of FIG. 22C.

In the fourth embodiment, as shown in FIGS. 22A and 22B, the clip unit 102 includes locking mechanisms 154 and 156 that are disposed inside the sheath 108 and positioned more proximally than the open end 222 of the sheath 108. The sheath 108 includes a recess (notch) 224 extending proximally from the open end 222 and having a U-shape. The recess/notch 224 in this invention is not limited to the U-shape, and may be any shape and size that is suitable for the recess/notch 224 to receive the locking mechanisms 154 and 156. The locking mechanisms 154 and 156 are engaged with a groove 192 that is formed on each of the pair of clip arms 112. The locking mechanism 154 and 156 each include a locking pin P that has a diameter larger than a width of the groove 192 so that the locking mechanisms 154 and 156 is slidable along the groove 192 without coming off the pair of clip arms 112.

The groove 192 may be shaped as a taper extending narrowly in the distal direction, and includes a reduced diameter portion 194 at a distal end portion thereof. By this configuration, as shown in FIGS. 22C and 22D, when the clip unit 102 is drawn proximally, the locking pin P moves distally with respect to the pair of clip arms 112 and makes the locking mechanisms 154 and 156 closer to each other. When the locking pin P arrives the reduced diameter portion 194, the locking pin P is locked at the reduced diameter portion 194 so as to prevent the locking mechanisms 154 and 156 from moving with respect to the pair of clip arms 112.

Since the locking mechanisms 154 and 156 are located inside the sheath 108 and more proximally than the open end 222 of the sheath 108, the target tissue 200 cannot enter into the sheath 108 because of the configuration of the open end 222 as described above. Thus, as the target tissue 200 is blocked by the open end 222 from entering into the sheath 108, the target tissue 200 can be prevented from being pinched between the locking mechanisms 154 and 156.

Exemplary Methods

An exemplary method for loading the clip unit 102 housed within the cartridge 106 to the applicator 104 comprises inserting the control member 110 and/or the sheath 108 of the applicator 104 through the proximal opening 174 of the cartridge 106. The distal end 118 of the control member 110 is moved with respect to the cartridge 106 by, for example, moving the spool 124 distally against the connector 116 until a distal force of the distal end 118 against the connector 116 exceeds a predetermined threshold value, deforming the proximal opening 164 of the slot 160 of the connector 116 to permit the distal end 118 to pass therethrough into the space 166 of the connector 116. As the distal end 118 is moved distally with respect to the sheath 108, the spool 124 may slide distally over the positioning feature 128 of the handle member 122, providing tactile feedback to the user that the distal end 118 of the control member 110 has been extended distally past the distal end 136 of the sheath 108 to be coupled to the connector 116. Once the distal end 118 is received within the space 166, the connector 116 reverts to its original shape, holding the distal end 118 therewithin. Upon coupling of the connector 116 and the control member 110, the clip unit 102 has been successfully loaded onto the applicator 104.

To remove the loaded clip unit 102 from the cartridge 106, the clip arms 112 are drawn proximally with respect to the sheath 108 of the applicator 104 to move the clip arms 112 toward the tissue gripping configuration, in which the restraining members 181 and 182 contact and are deform by each other as shown in FIG. 9A or cross each other as shown in FIG. 11A. The spool 124 may be drawn proximally with respect to the handle member 122 until the spool 124 is drawn proximally of the positioning feature 128. As described above, an interior surface of the lumen 138 of the sheath 108 constrains the clip arms 112 as they are drawn thereinto, to move the clip unit 102 toward the tissue gripping configuration. The clip unit 102 may then be drawn out of the cartridge 106 via the opening 174.

In use, after the clip unit 102 has been loaded onto the applicator 104, the clip unit 102 is inserted through the channel 230 (in FIG. 16) of an endoscope (or any other insertion device) and inserted into the body (e.g., through a natural body lumen) to a site adjacent to a target portion of tissue to be clipped. The clip unit 102 is inserted toward the target tissue 200 in the closed configuration to facilitate its passage through the channel 230. Upon reaching the site of the target tissue 200, the clip unit 102 is advanced out of the distal end 42 (in FIG. 17) of the channel 230 and the clip arms 112 are extended out of the sheath 108 of the applicator 104 to move the clip arms 112 toward the tissue receiving configuration by, for example, sliding the spool 124 distally over the handle member 122. Abutment of the distal surface 130 (in FIG. 6) of the spool 124 with the positioning feature 128 provides tactile feedback to the user, indicating that the clip arms 112 are at the maximum open configuration, and that moving the spool 124 any further distally would result in the connector 116 extending distally out of the sheath 108.

The clip arms 112 may be repeatedly moved between the tissue receiving and the tissue gripping configurations (the first and second configurations) until a target portion of tissue is received between the distal ends 140 of the clip arms 112, as desired. Once the target portion of tissue is received between the clip arms 112, the clip unit 102 is moved toward the tissue gripping configuration by moving the control member 110 proximally relative to the clip unit 102. At this time, the restraining member 180 is also activated to prevent the target portion of tissue from being pinched between the locking mechanisms 150 and 152 as described in the first through fourth embodiments.

When it is confirmed that the desired portion of tissue is gripped between the clip arms 112 (e.g., portions of tissue on opposite sides of a bleeding wound), the control member 110 is drawn further proximally relative to the clip unit 102 (via the spool 124) to lock the clip unit 102 in the closed configuration. That is, the clip arms 112 are drawn further proximally into the sheath 108 until the locking mechanisms 150, 152 engage one another, locking the clip arms 112 relative to one another. The control member 110 is drawn proximally with respect to the locking sheath 108 until the connector 116 comes into contact with and abuts the shoulder 176 of the lumen 138 of the sheath 108. The shoulder 176 prevents the connector 116 from moving proximally there past while a continued proximal force is exerted on the control member 110.

When the distal end 118 of the control member 110 exerts a force on the connector 116 beyond a predetermined threshold value, the connector 116 deforms (e.g., the proximal opening 164 expands) to permit the distal end 118 to be released from the longitudinal slot 160. Once the distal end 118 is released from the connector 116, the applicator 104 may be withdrawn from the living body, leaving the clip unit 102 including the restraining member 180 in the body over the target tissue. If so desired, a new clip unit 102 including the restraining member 180 is then loaded onto the applicator 104, in the same manner as described above, so that the device may then be used to clip a second portion of tissue. This process may be repeated using the same applicator 104 as many times as needed or desired.

Figure 23:
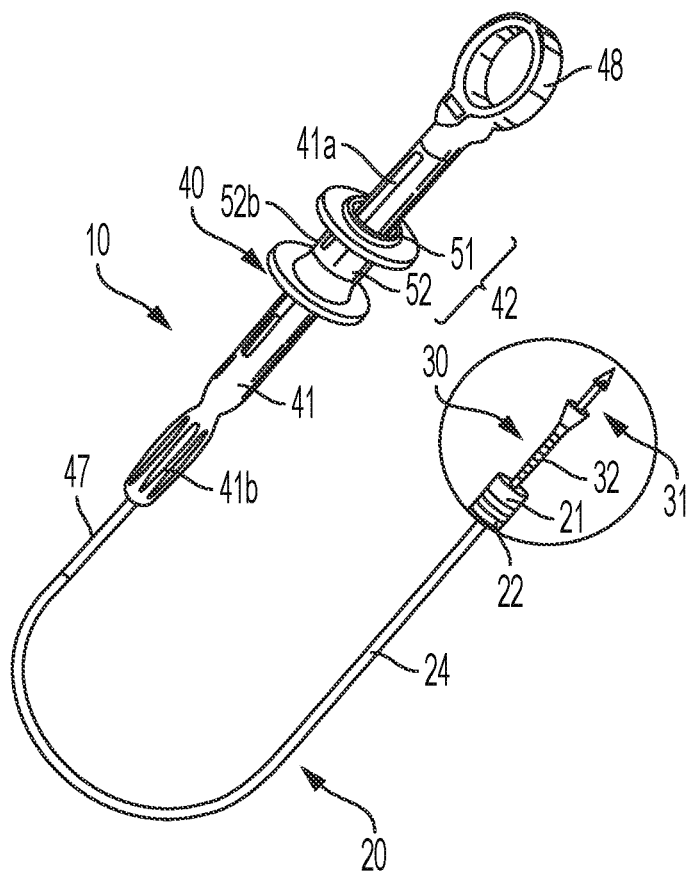
FIG. 23 is a perspective view schematically illustrating an applicator of an endoscope using a clip unit according to one exemplary embodiment.
Figure 24:
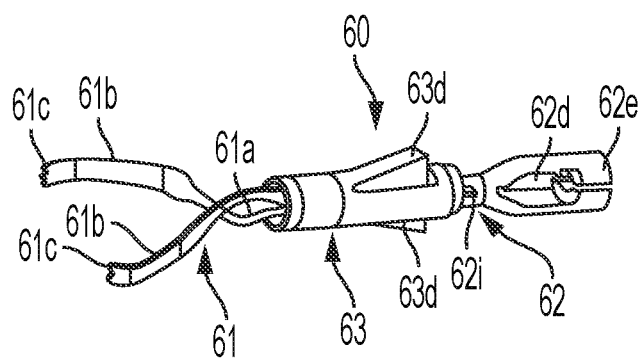
FIG. 24 is a perspective view schematically illustrating the clip unit to be associated with the applicator of FIG. 23.

The invention is not limited the above-described embodiments including connecting configurations between the clip unit 102 and the applicator 104. FIG. 23 is a perspective view schematically illustrating another connecting configuration in which an applicator of an endoscope to be used in combination with a clip unit according to one exemplary embodiment, and FIG. 24 is a perspective view schematically illustrating the clip unit to be used in combination with the applicator of FIG. 23.

As shown in FIG. 23, an applicator 10 is a unit for inserting into an abdominal cavity (a control unit), and may include an insertion tube 20, a control wire 30, and a control unit 40. The applicator 10 is used in combination with a clip unit 60, for example, by inserting into a surgical tool insertion channel (not shown) of an endoscope. Therefore, the insertion tube 20 includes a distal end tip 21, a distal end coil 22, and a proximal end coil 24. The control wire 30 includes a hook unit 31 at the distal end of the applicator 10 and wire 32. The control unit 40 includes a control unit main body 41, a slider 42, a supporter 47, and a thumb ring 18. The main body 41 includes a slit 41a and a grip 41b The slider 42 includes a first slide member 51 and a second slide member 52 with a slit 52b, As shown in FIG. 24, a clip unit 60 can be fit to the hook unit 31. The clip unit 60 may include a clip 61, a connection member 62, and a constraining pipe 63 as a tightening member. The clip 61 may have a loop (base) 61a made by bending a metallic plate material such as a flat spring made of stainless steel, for example, at substantially a central part. The clip 61 is crossed in vicinity of the loop 61a, and extended as a pair of clip arms 61b having an expanding characteristic in the state that the distal ends are separated. A tissue grasping part (a clip claw) 61c is formed at the end of the clip 61.

The crossing part of the arms 61b of the clip 61 is made narrower than the distal end side, and the tissue grasping parts 61c are opposed to each other. The clip 61 can slide on the inner surface of the constraining pipe 63 when moving the clip 61 in the direction of pulling into the pipe 63, but the clip 61 is engaged in the inner surface of the pipe 63 when moving the clip 61 in the direction reverse to the pulling-in direction.

The connection member 62 is formed by injection molding out of strong resin such, as liquid crystal polymer and polyamide synthetic fiber, for example. The connection member 62 is a cylindrical bar, and is engaged with the clip 61 inside the constraining pipe 63.

The connection member 62 includes a stopper projection 62i connected to the constraining pip 63, and the proximal end of the connection member 62 is forked into two branches that include a cutout 62d and an elastic arm 62e. The two branches are configured to receive the end of the arrowhead hook unit 31.

The constraining pipe 63 is formed by injection molding of rigid resin having appropriate elasticity, such as a material more flexible than the clip 61, for example, polyphthalamide (PPA) and polyamide (PA). By fitting the pipe 63 to the arms 61b of the clip 61, the arms 61b of the clip 61 are closed. The constraining pipe includes a pair of wings 63d elastically retractable in the radial direction is formed.

While preferred embodiments of the invention have been described and illustrated above, it should be understood that these are exemplary of the invention and are not to be considered as limiting. Additions, omissions, substitutions, and other modifications can be made without departing from the spirit and scope of the present invention. Accordingly, the invention is not to be considered as being limited by the foregoing description, and is only limited by the scope of the appended claims While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent.

Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

What is claimed is:

1. A clip device, comprising:
    a sheath;
    a plurality of clip arms movable between a first configuration in which the plurality of clip arms are opened to receive a target tissue, and a second configuration, in which the plurality of clip arms are closed to grip the target tissue;
    locking mechanisms respectively provided on the plurality of clip arms to engage one another for maintaining the second configuration; and
    a restraining mechanism configured to be associated with the locking mechanisms to prevent the target tissue from being pinched between the locking mechanisms, wherein the restraining mechanism includes a first restraining member and a second restraining member, distal end portions of which are respectively positioned more distally than the locking mechanisms, and
    wherein, in the second configuration, the first restraining member and the second restraining member contact each other and extend distally to push the target tissue away from the locking mechanisms.

2. The clip device according to claim 1, wherein the plurality of clip arms includes a first arm and a second arm; and the locking mechanisms are respectively disposed on inner surfaces of the first and second clip arms.

3. The clip device according to claim 2, wherein the first restraining member and the second restraining member cross each other in the second configuration and are each configured as a stopping bar to prevent the target tissue from being pinched between the locking mechanisms.

4. The clip device according to claim 2, wherein the first restraining member and the second restraining member are each configured as a curved bar having a protection front end surface.

5. The clip device according to claim 2, wherein the locking mechanisms include a first locking member and a second locking member, and
    wherein, in the first configuration, a first distance between the first restraining member and the second restraining member is less than a second distance between first locking member and the second locking member.

6. The clip device according to claim 2, wherein, in the first configuration, the first restraining member and the second restraining member are apart from each other at a first distance,
    wherein, in the second configuration, the first restraining member and the second restraining member are spaced apart from each other at a second distance, and
    wherein the second distance is smaller than the first distance.

7. The clip device according to claim 2, wherein the first arm and the second arm are configured to pivot about an axis and to rotate about the axis of the sheath.

8. The clip device according to claim 1, wherein the restraining mechanism is provided distally relative to the locking mechanisms.

9. The clip device according to claim 1, wherein the plurality of clip arms form a clip and wherein the locking mechanisms is configured to lock the clip in the second configuration.

10. The clip device according to claim 1, wherein, in the first configuration, a distal end of the restraining mechanism is provided distally relative to a distal end of the locking mechanisms.

11. The clip device according to claim 1, wherein the plurality of clip arms form a clip and wherein the clip device further comprises an operation wire inserted into the sheath and configured to translate the clip between the first configuration and the second configuration.

12. The clip device according to claim 11, wherein the operation wire is configured to be detachably attached to the plurality of clip arms.

13. The clip device according to claim 11, wherein the operation wire is configured to move along a longitudinal axis of the sheath and to protrude from a distal end of the sheath.

14. The clip device according to claim 1, wherein the restraining mechanism extends inwardly from an inner surface of the plurality of clip arms.

15. The clip device according to claim 1, wherein, in the first configuration, the locking mechanisms are located outside the sheath, and
    wherein, in the second configuration, the locking mechanisms are located inside the sheath.

16. The clip device according to claim 1, wherein the restraining mechanism are located with the locking mechanisms.

17. A clip device, comprising:
- a sheath including a lumen and at least one open end;
- a plurality of clip arms movable between a first configuration in which the plurality of clip arms are opened to receive a target tissue, and a second configuration, in which the plurality of clip arms are closed to grip the target tissue;
- locking mechanisms respectively provided on the plurality of clip arms to engage one another for maintaining the second configuration; and
- a restraining mechanism configured to be associated with the locking mechanisms to prevent the target tissue from being pinched between the locking mechanisms,
- wherein the plurality of clip arms includes a first arm and a second arm; and the locking mechanisms are respectively disposed on inner surfaces of the first and second clip arms,
- wherein the restraining mechanism includes a first restraining member and a second restraining member, distal end portions of which are respectively positioned more distally than the locking mechanisms, and
- wherein the first restraining member and the second restraining member contact each other and are deformed to extend distally in the second configuration, thereby pushing the target tissue away from the locking mechanisms.

18. A clip device, comprising:
- a sheath;
- a plurality of clip arms movable between a first configuration in which the plurality of clip arms are opened to receive a target tissue, and a second configuration, in which the plurality of clip arms are closed to grip the target tissue;
- locking mechanisms respectively provided on the plurality of clip arms to engage one another for maintaining the second configuration; and
- a restraining mechanism configured to be associated with the locking mechanisms to prevent the target tissue from being pinched between the locking mechanisms,
- wherein the restraining mechanism includes a first restraining member and a second restraining member, distal end portions of which are respectively positioned more distally than the locking mechanisms, and
- wherein, in the second configuration, the first restraining member and the second restraining member contact each other and are each deformed distally to push the target tissue away from the locking mechanisms.

* * * * *